(12) United States Patent
Peakman et al.

(10) Patent No.: US 8,906,383 B2
(45) Date of Patent: Dec. 9, 2014

(54) T CELL RECEPTOR HAVING BINDING AFFINITY FOR A PEPTIDE-MHC COMPLEX AND USES THEREOF

(75) Inventors: Mark Peakman, London (GB); Ruben Varela Calvino, Santiago de Compostela (ES)

(73) Assignee: King's College London, London (GB)

( * ) Notice: Subject to any disclaimer, the term of this patent is extended or adjusted under 35 U.S.C. 154(b) by 894 days.

(21) Appl. No.: 12/666,416

(22) PCT Filed: Jun. 27, 2008

(86) PCT No.: PCT/GB2008/002223
§ 371 (c)(1),
(2), (4) Date: Mar. 24, 2010

(87) PCT Pub. No.: WO2009/004315
PCT Pub. Date: Jan. 8, 2009

(65) Prior Publication Data
US 2010/0297011 A1    Nov. 25, 2010

(30) Foreign Application Priority Data

Jun. 29, 2007 (GB) .................................. 0712670.9

(51) Int. Cl.
*A61K 39/00* (2006.01)
*G01N 33/50* (2006.01)
*G01N 33/68* (2006.01)
*C07K 7/06* (2006.01)
*C07K 14/62* (2006.01)
*A61K 38/00* (2006.01)

(52) U.S. Cl.
CPC .............. *C07K 14/62* (2013.01); *G01N 33/505* (2013.01); *A61K 38/00* (2013.01); *G01N 2800/042* (2013.01); *G01N 33/6893* (2013.01); *C07K 7/06* (2013.01)
USPC ...................................................... 424/192.1

(58) Field of Classification Search
None
See application file for complete search history.

(56) References Cited

U.S. PATENT DOCUMENTS

2004/0234531 A1   11/2004 Casares et al.

FOREIGN PATENT DOCUMENTS

| WO | 2004/050705 A2 | 6/2004 |
| WO | 2005/073248 A1 | 8/2005 |
| WO | 2006/007667 A1 | 1/2006 |

OTHER PUBLICATIONS

Chang, L., et al. Tissue Antigens. 2003;62:408-417.*
Bulek et al., "Structural basis for the killing of human beta cells by CD8+T cells in type 1 diabetes," Nature Immunology, Mar. 2012, vol. 13:3, pp. 283-290.
Li et al., "Directed evolution of human T-cell receptors with picomolar affinities by phage display," Nature Biotechnology, Mar. 2005, vol. 23:3, pp. 349-354.
Varela-Calvino et al., "T Cell Activation by Coxsackievirus B4 Antigens in Type 1 Diabetes Mellitus: Evidence for Selective TCR Vb Usage Without Superantigenic Activity," J Immunol, 2001, vol. 167, pp. 3513-3520.
Varela-Calvino et al., "Characterization of the T-Cell Response to Coxsackievirus B4—Evidence That Effector Memory Cells Predominate in Patients With Type 1 Diabetes," Diabetes, Jun. 2002, vol. 51, pp. 1745-1753.
Arif et al., "Autoreactive T cell responses show proinflammatory polarization in diabetes but a regulatory phenotype in health," Journal of Clinical investigation, 2004, vol. 113:3, pp. 451-463.
Varela-Calvino et al., "Identification of a Naturally Processed Cytoxic CD8 T-Cell Epitope of Coxsackievirus B4, Presented by HLA-A2.1 and Located in the PEVKEK Region of the P2C Nonstructural Protein," Journal of Virology, 2004, vol. 78:24, pp. 13399-13408.
Lindley et al., "Defective Suppressor Function in CD4+CD25+T-Cells From Patients With Type 1 Diabetes," Diabetes, Jan. 2005, vol. 54, pp. 92-99.
Lozanoska-Ochser et al. "Atorvastatin Fails to Prevent the Development of Autoimmune Diabetes Despite Inhibition of Phathogenic B-Cell-Specific CD8 T-Cells," Diabetes, Apr. 2006, vol. 55, ppl. 1004-1010.
Zanone et al., "Human pancreatic islet endothelial cells express coxsackievirus and adenovirus receptor and are activated by coxsackie B virus infection," The FASEB Journal, 2007, vol. 21.
Chang et al., "Novel strategy for identification of candidate cytotoxic T-cell epitopes from human preproinsulin," Tissue Antigens, 2003, vol. 62, pp. 408-417.
Congia et al., "T cell epitopes of insulin defined in HLA-DR4 transgenic mice are derived from preproinsulin and proinsulin," Proc. Natl. Acad. Sci. USA, 1998, vol. 95, pp. 3833-3838.
Ellis et al., "HLA class II molecules on haplotypes associtaed with type 1 diabetes exhibit similar patterns of binding affinities for coxsackievirus P2C peptides," Immunology, 2005, vol. 116, pp. 337-346.
Astill et al., "Promiscuous binding of proinsulin peptides to Type 1 diabetes-permissive and -protective HLA class II molecules, " Diabetologia, 2003, vol. 46, pp. 46-503.

(Continued)

*Primary Examiner* — Gerald R Ewoldt
(74) *Attorney, Agent, or Firm* — Stites & Harbison PLLC; Mandy Wilson Decker

(57) ABSTRACT

The present disclosure provides isolated preproinsulin-derived peptides of 8 or 9 amino acids, comprising the amino acid sequence WGPDPAA (SEQ ID NO: 1), isolated Class I peptide-HLA complexes presenting said peptides and isolated molecules having binding affinity for said peptides and/or said peptide-HLA complexes. Such compositions are useful in the treatment of type 1 diabetes mellitus (T1DM). Such isolated molecules can include a T cell receptor (TCR) having specific binding affinity for a peptide-MHC complex wherein the MHC is an HLA Class I molecule and the peptide is a preproinsulin-derived peptide of 8 to 10 amino acids, comprising the amino acid sequence WGPDPAA (SEQ ID NO: 1).

13 Claims, 18 Drawing Sheets

(56) References Cited

OTHER PUBLICATIONS

Rathmann et al., "Preproinsulin-Specific CD8+ T Cells Secrete IFNγ in Human Type 1 Diabetes," Ann. N.Y. Acad. Sci., 2004, vol. 1037, pp. 22-25.

Altamirano et al., "Oxidative refolding chromatography: folding of the scorpion toxin Cn5," nature Biotechnology, 1999, vol. 17, pp. 187-191.

Altamirano et al., "Refolding chromatography with immobilized mini-chaperones," Proc. Natl. Acad. Sci. USA, 1997 vol. 94, pp. 3576-3578.

Boulter et al., "Stable, soluble T-cell receptor molecules for crystallization and therapeutics," Protein Engineering, 2003, vol. 16:9, pp. 707-711.

Masteller et al., "Immunotherapy of insulin-dependent diabetes mellitus," Current Opinion in Immunology, 2002, vol. 14, pp. 652-659.

Peakman et al., "Naturally processed and presented epitopes of the islet cell autoantigen IA-2 eluted from HLA-DR4," J. Clin. Invest., 1999, vol. 104, pp. 1449-1457.

Peakman et al., "Characterization of Preparations of GAD65, Proinsulin, and the Islet Tyrosine Phosphatase IA-2 for use in Detection of Autoreactive T-Cells in Type 1 Diabetes," Diabetes, 2001, vol. 50, pp. 1749-1754.

Greening et al., "Processing and Presentation of the Islet Autoantigen GAD by Vascular Endothelial Cells Promotes Transmigration of Autoreactive T-Cells," Diabetes, 2003, vol. 52, pp. 717-725.

* cited by examiner

Figure 1

MALWMRLLPLLALLALWGPDPAAAFVNQHLCGSHLVEALYLVCGERGFFYTPKTRREA

EDLQVGQVELGGGPGAGSLQPLALEGSLQKR*GIVEQCCTSICSLYQLENYCN*

(SEQ ID NO: 19)

| # | Immon. | a | a⁰ | b | b⁰ | Seq. | y | y⁰ | # |
|---|--------|-----|-----|-----|-----|------|--------|--------|---|
| 1 | 159.09 | 159.09 | | 187.09 | | W | | | 8 |
| 2 | 30.03 | 216.11 | | 244.11 | | G | 598.28 | 580.27 | 7 |
| 3 | 70.07 | 313.17 | | 341.16 | | P | 541.26 | 523.25 | 6 |
| 4 | 88.04 | 428.19 | 410.18 | 456.19 | 438.18 | D | 444.21 | 426.20 | 5 |
| 5 | 70.07 | 525.25 | 507.24 | 553.24 | 535.23 | P | 329.18 | | 4 |
| 6 | 44.05 | 596.28 | 578.27 | 624.28 | 606.27 | A | 232.13 | | 3 |
| 7 | 44.05 | 667.32 | 649.31 | 695.31 | 677.30 | A | 161.09 | | 2 |
| 8 | 44.05 | | | | | A | 90.05 | | 1 |

Figure 10 gatctcgatcccgcgaaattaatacgactcactatagggagaccacaacggtttccctctagaaataattttgtttaactttaaga
aggagatatacatatgggatccatggtaagcttgaattccgatccggctgctaacaaagcccgaaaggaagctgagttggct
gctgccaccgctgagcaataactagcataaccccttggggcctctaaacgggtcttgaggggttttttgctgaaaggaggaa
ctatatccggataattcttgaagacgaaagggcctcgtgatacgcctatttttataggttaatgtcatgataataatggtttcttag
acgtcaggtggcacttttcggggaaatgtgcgcggaacccctatttgtttattttctaaatacattcaaatatgtatccgctcatg
agacaataaccctgataaatgcttcaataatattttgttaaaattcgcgttaaattttgttaaatcagctcatttttaaccaatagg
ccgaaatcggcaaaatcccttataaatcaaaagaatagaccgagatagggttgagtgttgttccagtttggaacaagagtcca
ctattaaagaacgtggactccaacgtcaaagggcgaaaaaccgtctatcagggcgatggcccactacgtgaaccatcaccc
taatcaagttttttggggtcgaggtgccgtaaagcactaaatcggaacctaaagggagccccgatttagagcttgacggg
gaaagccggcgaacgtggcgagaaaggaagggaagaaagcgaaaggagcgggcgctagggcgctggcaagtgtagc
ggtcacgctgcgcgtaaccaccacacccgccgcgcttaatgcgccgctacagggcgcgtcaggtggcacttttcggggaa
atgtgcgcggaacccctatttgtttattttctaaatacattcaaatatgtatccgctcatgagacaataaccctgataaatgcttca
ataatattgaaaaaggaagagtatgagtattcaacatttccgtgtcgcccttattccctttttttgcggcattttgccttcctgttttg
ctcacccagaaacgctggtgaaagtaaaagatgctgaagatcagttgggtgcacgagtgggttacatcgaactggatctca
acagcggtaagatccttgagagttttcgccccgaagaacgttttccaatgatgagcacttttaaagttctgctatgtggcgcggt
attatcccgtgttgacgccgggcaagagcaactcggtcgccgcatacactattctcagaatgacttggttgagtactcaccag
tcacagaaaagcatcttacggatggcatgacagtaagagaattatgcagtgctgccataaccatgagtgataacactgcggc
caacttacttctgacaacgatcggaggaccgaaggagctaaccgcttttttgcacaacatgggggatcatgtaactcgccttg
atcgttgggaaccggagctgaatgaagccataccaaacgacgagcgtgacaccacgatgcctgcagcaatggcaacaac
gttgcgcaaactattaactggcgaactacttactctagcttcccggcaacaattaatagactggatggaggcggataaagttg
caggaccacttctgcgctcgcccttccggctggctggtttattgctgataaatctggagccggtgagcgtgggtctcgcggt
atcattgcagcactggggccagatggtaagccctcccgtatcgtagttatctacacgacggggagtcaggcaactatggatg
aacgaaatagacagatcgctgagataggtgcctcactgattaagcattggtaactgtcagaccaagtttactcatatatacttta
gattgatttaaaacttcattttaatttaaaaggatctaggtgaagatcctttttgataatctcatgaccaaaatcccttaacgtgagt
tttcgttccactgagcgtcagaccccgtagaaaagatcaaaggatcttcttgagatcctttttttctgcgcgtaatctgctgcttgc
aaacaaaaaaaccaccgctaccagcggtggtttgtttgccggatcaagagctaccaactctttttccgaaggtaactggcttc
agcagagcgcagataccaaatactgtccttctagtgtagccgtagttaggccaccacttcaagaactctgtagcaccgcctac
atacctcgctctgctaatcctgttaccagtggctgctgccagtggcgataagtcgtgtcttaccgggttggactcaagacgata
gttaccggataaggcgcagcggtcgggctgaacggggggttcgtgcacacagcccagcttggagcgaacgacctacacc
gaactgagatacctacagcgtgagctatgagaaagcgccacgcttcccgaagggagaaaggcggacaggtatccggtaa
gcggcagggtcggaacaggagagcgcacgagggagcttccaggggaaacgcctggtatctttatagtcctgtcgggttt
cgccacctctgacttgagcgtcgatttttgtgatgctcgtcaggggggcggagcctatggaaaaacgccagcaacgcggcc
tttttacggttcctggccttttgctggccttttgctcacatgttctttcctgcgttatcccctgattctgtggataaccgtattaccgcc
tttgagtgagctgataccgctcgccgcagccgaacgaccgagcgcagcgagtcagtgagcgaggaagcggaagagcgc
ctgatgcggtattttctccttacgcatctgtgcggtatttcacaccgcaatggtgcactctcagtacaatctgctctgatgccgca
tagttaagccagtatacactccgctatcgctacgtgactgggtcatggctgcgccccgacacccgccaacacccgctgacg
cgccctgacgggcttgtctgctcccggcatccgcttacagacaagctgtgaccgtctccgggagctgcatgtgtcagaggtt
ttcaccgtcatcaccgaaacgcgcgaggcag (SEQ ID NO: 20)

Figure 11 gatctcgatcccgcgaaattaatacgactcactatagggagaccacaacggtttccctctagaaataattttgtttaactttaaga
aggagatataatcgatgtctaactcgagtgacaagtctgtctgcctattcaccgattttgattctcaaacaaatgtgtcacaaagt
aaggattctgatgtgtatatcacagacaaatgtgtgctagacatgaggtctatggacttcaagagcaacagtgctgtggcctg
gagcaacaaatctgactttgcatgtgcaaacgccttcaacaacagcattattccagaagacaccttcttccccagcccagaaa
gttcctaagcttgaattccgatccggctgctaacaaagcccgaaaggaagctgagttggctgctgccaccgctgagcaataa
ctagcataaccccttggggcctctaaacgggtcttgaggggttttttgctgaaaggaggaactatatccggataattcttgaag
acgaaagggcctcgtgatacgcctatttttataggttaatgtcatgataataatggtttcttagacgtgaggtggcactttttcggg
gaaatgtgcgcggaaccccatttgtttattttttctaaatacattcaaatatgtatccgctcatgagacaataaccctgataaatgc
ttcaataatattttgttaaaattcgcgttaaattttttgttaaatcagctcattttttaaccaataggccgaaatcggcaaaatcccttat
aaatcaaaagaatagaccgagatagggttgagtgttgttccagtttggaacaagagtccactattaaagaacgtggactccaa
cgtcaaagggcgaaaaaccgtctatcagggcgatggcccactacgtgaaccatcaccctaatcaagttttttggggtcgagg
tgccgtaaagcactaaatcggaaccctaaagggagccccgatttagagcttgacggggaaagccggcgaacgtggcga
gaaaggaagggaagaaagcgaaaggagcgggcgctagggcgctggcaagtgtagcggtcacgctgcgcgtaaccacc
acacccgccgcgcttaatgcgccgctacagggcgcgtcaggtggcacttttcggggaaatgtgcgcggaaccccctatttgtt
tatttttctaaatacattcaaatatgtatccgctcatgagacaataaccctgataaatgcttcaataatattgaaaaaggaagagta
tgagtattcaacatttccgtgtcgcccttattcccttttttgcggcattttgccttcctgttttttgctcacccagaaacgctggtgaaa
gtaaaagatgctgaagatcagttgggtgcacgagtgggttacatcgaactggatctcaacagcggtaagatccttgagagttt
tcgccccgaagaacgttttccaatgatgagcacttttaaagttctgctatgtggcgcggtattatcccgtgttgacgccgggca
agagcaactcggtcgccgcatacactattctcagaatgacttggttgagtactcaccagtcacagaaaagcatcttacggatg
gcatgacagtaagagaattatgcagtgctgccataaccatgagtgataacactgcggccaacttacttctgacaacgatcgg
aggaccgaaggagctaaccgcttttttgcacaacatgggggatcatgtaactcgccttgatcgttgggaaccggagctgaat
gaagccataccaaacgacgagcgtgacaccacgatgcctgcagcaatggcaacaacgttgcgcaaactattaactggcga
actacttactctagcttcccggcaacaattaatagactggatggaggcggataaagttgcaggaccacttctgcgctcggccc
ttccggctggctggtttattgctgataaatctggagccggtgagcgtgggtctcgcggtatcattgcagcactggggccagat
ggtaagccctcccgtatcgtagttatctacacgacggggagtcaggcaactatggatgaacgaaatagacagatcgctgag

Figure 11 (Cont.)

ataggtgcctcactgattaagcattggtaactgtcagaccaagtttactcatatatactttagattgatttaaaacttcatttttaattt
aaaaggatctaggtgaagatccttttgataatctcatgaccaaaatcccttaacgtgagttttcgttccactgagcgtcagacc
ccgtagaaaagatcaaaggatcttcttgagatcctttttttctgcgcgtaatctgctgcttgcaaacaaaaaaaccaccgctacc
agcggtggtttgtttgccggatcaagagctaccaactctttttccgaaggtaactggcttcagcagagcgcagataccaaata
ctgtccttctagtgtagccgtagttaggccaccacttcaagaactctgtagcaccgcctacatacctcgctctgctaatcctgtt
accagtggctgctgccagtggcgataagtcgtgtcttaccgggttggactcaagacgatagttaccggataaggcgcagcg
gtcgggctgaacggggggttcgtgcacacagcccagcttggagcgaacgacctacaccgaactgagatacctacagcgt
gagctatgagaaagcgccacgcttcccgaagggagaaaggcggacaggtatccggtaagcggcagggtcggaacagg
agagcgcacgagggagcttccaggggggaaacgcctggtatctttatagtcctgtcgggtttcgccacctctgacttgagcgt
cgattttgtgatgctcgtcagggggggcggagcctatggaaaaacgccagcaacgcggcctttttacggttcctggccttttg
ctggccttttgctcacatgttctttcctgcgttatcccctgattctgtggataaccgtattaccgcctttgagtgagctgataccgct
cgccgcagccgaacgaccgagcgcagcgagtcagtgagcgaggaagcggaagagcgcctgatgcggtattttctcctta
cgcatctgtgcggtatttcacaccgcaatggtgcactctcagtacaatctgctctgatgccgcatagttaagccagtatacact
ccgctatcgctacgtgactgggtcatggctgcgccccgacacccgccaacacccgctgacgcgccctgacgggcttgtct
gctcccggcatccgcttacagacaagctgtgaccgtctccgggagctgcatgtgtcagaggttttcaccgtcatcaccgaaa
cgcgcgaggcag (SEQ ID NO: 21)

Figure 12 gatctcgatcccgcgaaattaatacgactcactatagggagaccacaacggtttccctctagaaataattttgtttaactttaaga
aggagatatacatatgaacgctggtgtcactcagaccccaaaattccaggtcctgaagacaggacagagcatgacactgca
gtgtgcccaggatatgaaccatgaatacatgtcctggtatcgacaagacccaggcatggggctgaggctgattcattactca
gttggtgctggtatcactgaccaaggagaagtccccaatggctacaatgtctccagatcaaccacagaggatttcccgctca
ggctgctgtcggctgctccctcccagacatctgtgtacttctgtgccagcaggccgggactagcgggagggcgaccagag
cagtacttcgggccgggcaccaggctcacggtcacagaggacctgaaaaacgtgttcccacccgaggtcgctgtgtttga
gccatcagaagcagagatctcccacacccaaaaggccacactggtgtgcctggccaccggtttctaccccgaccacgtgg
agctgagctggtgggtgaatgggaaggaggtgcacagtggggtctgcacagacccgcagcccctcaaggagcagcccg
ccctcaatgactccagatacgctctgagcagccgcctgagggtctcggccaccttctggcaggaccccgcaaccacttcc
gctgtcaagtccagttctacgggctctcggagaatgacgagtggacccaggatagggccaaacccgtcacccagatcgtc
agcgccgaggcctggggtagagcagactaagcttgaattccgatccggctgctaacaaagcccgaaaggaagctgagttg
gctgctgccaccgctgagcaataactagcataaccccttggggcctctaaacgggtcttgaggggttttttgctgaaaggag
gaactatatccggataattcttgaagacgaaagggcctcgtgatacgcctatttttataggttaatgtcatgataataatggtttct
tagacgtcaggtggcactttcggggaaatgtgcgcggaacccctatttgtttatttttctaaatacattcaaatatgtatccgctc
atgagacaataaccctgataaatgcttcaataatattttgttaaaattcgcgttaaattttgttaaatcagctcatttttttaaccaata
ggccgaaatcggcaaaatcccttataaatcaaaagaatagaccgagatagggttgagtgttgttccagtttggaacaagagt
ccactattaaagaacgtggactccaacgtcaaagggcgaaaaaccgtctatcagggcgatggcccactacgtgaaccatca
ccctaatcaagttttttggggtcgaggtgccgtaaagcactaaatcggaacccctaaagggagcccccgatttagagcttgac
ggggaaagccggcgaacgtggcgagaaaggaagggaagaaagcgaaaggagcgggcgctagggcgctggcaagtg
tagcggtcacgctgcgcgtaaccaccacacccgccgcgcttaatgcgccgctacagggcgcgtcaggtggcactttcgg
ggaaatgtgcgcggaacccctatttgtttatttttctaaatacattcaaatatgtatccgctcatgagacaataaccctgataaatg
cttcaataatattgaaaaaggaagagtatgagtattcaacatttccgtgtcgcccttattccttttttgcggcatttttgccttcctgt
ttttgctcacccagaaacgctggtgaaagtaaaagatgctgaagatcagttgggtgcacgagtgggttacatcgaactggat
ctcaacagcggtaagatccttgagagttttcgccccgaagaacgttttccaatgatgagcacttttaaagttctgctatgtggcg
cggtattatcccgtgttgacgccgggcaagagcaactcggtcgccgcatacactattctcagaatgacttggttgagtactca
ccagtcacagaaaagcatcttacggatggcatgacagtaagagaattatgcagtgctgccataaccatgagtgataacactg
cggccaacttacttctgacaacgatcggaggaccgaaggagctaaccgcttttttgcacaacatgggggatcatgtaactcg
ccttgatcgttgggaaccggagctgaatgaagccataccaaacgacgagcgtgacaccacgatgcctgcagcaatggcaa
caacgttgcgcaaactattaactggcgaactacttactctagcttcccggcaacaattaatagactggatggaggcggataaa
gttgcaggaccacttctgcgctcggcccttccggctggctggtttattgctgataaatctggagccggtgagcgtgggtctcg
cggtatcattgcagcactggggccagatggtaagccctcccgtatcgtagttatctacacgacggggagtcaggcaactatg
gatgaacgaaatagacagatcgctgagataggtgcctcactgattaagcattggtaactgtcagaccaagtttactcatatata
ctttagattgatttaaaacttcatttttaatttaaaaggatctaggtgaagatcctttttgataatctcatgaccaaaatcccttaacgt
gagttttcgttccactgagcgtcagacccccgtagaaaagatcaaaggatcttcttgagatcctttttttctgcgcgtaatctgctg
cttgcaaacaaaaaaaccaccgctaccagcggtggtttgtttgccggatcaagagctaccaactctttttccgaaggtaactg
gcttcagcagagcgcagataccaaatactgtccttctagtgtagccgtagttaggccaccacttcaagaactctgtagcaccg
cctacatacctcgctctgctaatcctgttaccagtggctgctgccagtggcgataagtcgtgtcttaccgggttggactcaaga
cgatagttaccggataaggcgcagcggtcgggctgaacggggggttcgtgcacacagcccagcttggagcgaacgacct

Figure 12 (Cont.)

acaccgaactgagatacctacagcgtgagctatgagaaagcgccacgcttcccgaagggagaaaggcggacaggtatcc
ggtaagcggcagggtcggaacaggagagcgcacgagggagcttccagggggaaacgcctggtatctttatagtcctgtc
gggtttcgccacctctgacttgagcgtcgattttgtgatgctcgtcagggggcggagcctatggaaaaacgccagcaacg
cggccttttacggttcctggccttttgctggccttttgctcacatgttctttcctgcgttatcccctgattctgtggataaccgtatta
ccgcctttgagtgagctgataccgctcgccgcagccgaacgaccgagcgcagcgagtcagtgagcgaggaagcggaag
agcgcctgatgcggtatttctccttacgcatctgtgcggtatttcacaccgcaatggtgcactctcagtacaatctgctctgatg
ccgcatagttaagccagtatacactccgctatcgctacgtgactgggtcatggctgcgccccgacacccgccaacacccgc
tgacgcgccctgacgggcttgtctgctcccggcatccgcttacagacaagctgtgaccgtctccgggagctgcatgtgtcag
aggttttcaccgtcatcaccgaaacgcgcgaggcag (SEQ ID NO: 22)

Figure 13 gatctcgatcccgcgaaattaatacgactcactatagggagaccacaacggtttccctctagaaataattttgtttaactttaaga
aggagatatacatatgtctaactcgagtgacaagtctgtctgcctattcaccgattttgattctcaaacaaatgtgtcacaaagta
aggattctgatgtgtatatcacagacaaatgtgtgctagacatgaggtctatggacttcaagagcaacagtgctgtggcctgg
agcaacaaatctgactttgcatgtgcaaacgccttcaacaacagcattattccagaagacaccttcttccccagcccagaaag
ttcctaagcttgaattccgatccggctgctaacaaagcccgaaaggaagctgagttggctgctgccaccgctgagcaataac
tagcataaccccttggggcctctaaacgggtcttgagggggttttttgctgaaaggaggaactatatccggataattcttgaaga
cgaaagggcctcgtgatacgcctatttttataggttaatgtcatgataataatggtttcttagacgtcaggtggcacttttcgggg
aaatgtgcgcggaaccccctatttgtttattttctaaatacattcaaatatgtatccgctcatgagacaataaccctgataaatgctt
caataatattttgttaaaattcgcgttaaattttgttaaatcagctcatttttaaccaataggccgaaatcggcaaaatcccttata
aatcaaaagaatagaccgagatagggttgagtgttgttccagtttggaacaagagtccactattaaagaacgtggactccaac
gtcaaagggcgaaaaaccgtctatcagggcgatggcccactacgtgaaccatcaccctaatcaagttttttggggtcgaggt
gccgtaaagcactaaatcggaacccaaagggagccccgatttagagcttgacggggaaagccggcgaacgtggcga
gaaaggaagggaagaaagcgaaaggagcgggcgctagggcgctggcaagtgtagcggtcacgctgcgcgtaaccacc
acacccgccgcgcttaatgcgccgctacagggcgcgtcaggtggcacttttcgggaaatgtgcgcggaaccccctatttgtt
tattttctaaatacattcaaatatgtatccgctcatgagacaataaccctgataaatgcttcaataatattgaaaaaggaagagta
tgagtattcaacatttccgtgtcgcccttattccttttttgcggcatttttgccttcctgttttgctcacccagaaacgctggtgaaa
gtaaaagatgctgaagatcagttgggtgcacgagtgggttacatcgaactggatctcaacagcggtaagatccttgagagttt
tcgccccgaagaacgttttccaatgatgagcacttttaaagttctgctatgtggcgcggtattatcccgtgttgacgccgggca
agagcaactcggtcgccgcatacactattctcagaatgacttggttgagtactcaccagtcacagaaaagcatcttacggatg
gcatgacagtaagagaattatgcagtgctgccataaccatgagtgataacactgcggccaacttacttctgacaacgatcgg
aggaccgaaggagctaaccgcttttttgcacaacatgggggatcatgtaactcgccttgatcgttgggaaccggagctgaat
gaagccataccaaacgacgagcgtgacaccacgatgcctgcagcaatggcaacaacgttgcgcaaactattaactggcga
actacttactctagcttcccggcaacaattaatagactggatggaggcggataaagttgcaggaccacttctgcgctcggccc
ttccggctggctggtttattgctgataaatctggagccggtgagcgtgggtctcgcggtatcattgcagcactggggccagat
ggtaagccctcccgtatcgtagttatctacacgacggggagtcaggcaactatggatgaacgaaatagacagatcgctgag
ataggtgcctcactgattaagcattggtaactgtcagaccaagtttactcatatatactttagattgatttaaaacttcattttaattt
aaaaggatctaggtgaagatcctttttgataatctcatgaccaaaatcccttaacgtgagttttcgttccactgagcgtcagacc
ccgtagaaaagatcaaaggatcttcttgagatccttttttctgcgcgtaatctgctgcttgcaaacaaaaaaaccaccgctacc
agcggtggtttgtttgccggatcaagagctaccaactctttttccgaaggtaactggcttcagcagagcgcagataccaaata
ctgtccttctagtgtagccgtagttaggccaccacttcaagaactctgtagcaccgcctacatacctcgctctgctaatcctgtt
accagtggctgctgccagtggcgataagtcgtgtcttaccgggttggactcaagacgatagttaccggataaggcgcagcg
gtcgggctgaacggggggttcgtgcacacagcccagcttggagcgaacgacctacaccgaactgagatacctacagcgt
gagctatgagaaagcgccacgcttcccgaagggagaaaggcggacaggtatccggtaagcggcagggtcggaacagg
agagcgcacgagggagcttccagggggaaacgcctggtatctttatagtcctgtcgggtttcgccacctctgacttgagcgt
cgatttttgtgatgctcgtcaggggggcggagcctatggaaaaacgccagcaacgcggcctttttacggttcctggccttttg
ctggccttttgctcacatgttctttcctgcgttatcccctgattctgtggataaccgtattaccgcctttgagtgagctgataccgct
cgccgcagccgaacgaccgagcgcagcgagtcagtgagcgaggaagcggaagagcgcctgatgcggtattttctccta
cgcatctgtgcggtatttcacaccgcaatggtgcactctcagtacaatctgctctgatgccgcatagttaagccagtatacact
ccgctatcgctacgtgactgggtcatggctgcgccccgacacccgccaacacccgctgacgcgccctgacgggcttgtct
gctcccggcatccgcttacagacaagctgtgaccgtctccgggagctgcatgtgtcagaggttttcaccgtcatcaccgaaa
cgcgcgaggcag (SEQ ID NO: 23)

T CELL RECEPTOR HAVING BINDING AFFINITY FOR A PEPTIDE-MHC COMPLEX AND USES THEREOF

The present invention relates to certain preproinsulin-derived peptides, to molecules, such as T cell receptors and antibodies, with specific binding affinity for such peptides or class I HLA-peptide complexes presenting such peptides, and to aspects of the preparation and use of such peptides and binding molecules, for example in the treatment of type 1 diabetes mellitus.

BACKGROUND TO THE INVENTION

Type 1 diabetes mellitus (T1DM) is an auto immune disease characterised by metabolic dysfunction, most notably dysregulation of glucose metabolism, accompanied by characteristic long-term vascular and neurological complications. T1DM is one of the commonest autoimmune diseases, affecting one in 250 individuals in the US where there are approximately 10,000 to 15,000 new cases reported each year, and the incidence is rising. The highest prevalence of T1DM is found in northern Europe, where more than 1 in every 150 Finns develops T1DM by the age of 15. In contrast, T1DM is less common in black and Asian populations where the frequency is less than half that among the white population.

T1DM is characterised by absolute insulin deficiency, making patients dependent on exogenous insulin for survival. Prior to the acute clinical onset of T1DM with symptoms of hyperglycaemia there is a long asymptomatic preclinical period, during which insulin-producing beta cells are progressively destroyed. The autoimmune destruction of beta cells ($\beta$ cells) is associated with lymphocytic infiltration. In addition, abnormalities in the presentation of MHC Class I antigens on the cell surface have been identified in both animal models and in human T1DM. This immune abnormality may explain why humans become intolerant of self-antigens although it is not clear why only beta cells are preferentially destroyed.

There is a need for new means of treating T1DM, which the substances and methods described herein will address.

There is ample evidence that CD8 cells are involved in the disease process that leads to T1DM. Histological analysis of the islets in an affected individual shows infiltration by CD8 T cells. In animal models of T1DM, the disease process may be transferred from a diseased animal to a healthy animal using CD8 T cells. There is a genetic association between the development of T1DM and certain HLA class I molecules that are critical for CD8 target recognition. Finally, activated CD8 T cells are present in the circulation of high-risk subjects who develop T1DM.

There is an emerging interest in defining the peptide epitopes recognised by CD8 T cells involved in anti-islet autoimmune responses. Identification of epitopes is important for understanding mechanisms of disease development, developing laboratory assays to monitor islet damage and designing therapeutic interventions to halt disease.

The peptide epitopes that form complexes with HLA class I molecules are derived from proteins in the cell cytosol. In the case of an autoimmune disease like T1DM, it can be assumed that the proteins are specific to the cell targeted in the disease. In addition, the epitopes are likely to be from a protein known, from other evidence, to be involved in the autoimmune process as a target (termed an autoantigen). A protein called preproinsulin fits these criteria. It is specific to the $\beta$ cells destroyed in T1DM. Preproinsulin (PPI) is a precursor protein that gives rise to insulin. Insulin is present in storage granules that occupy most of the $\beta$ cell cytosol. Insulin is known to be the target of the autoimmune process in T1DM from studies showing the presence of insulin-specific autoantibodies and autoreactive CD4 T cells in most patients who develop the disease. As yet, there are no data on the epitopes of PPI that may be used as targets by CD8 T cells in T1DM.

Previously, methods have been used to try to identify epitopes. At least three approaches have been used previously:

1. Epitope prediction. Most HLA class I molecules have a "preferred" configuration of peptides to which they can bind, termed a "motif". There are publicly available applications that enable one to search a protein for stretches of sequence that carry the required motif. However, this approach provides no information about whether the epitopes identified are actually generated in vivo. Many peptides have the capability to bind to a class I HLA molecule, so this approach generates many false positives.

2. Generating CD8 T cells. This approach involves cloning CD8 cells that react with a particular protein or peptide. The approach is successful in patients with acute virus infections, where the number of CD8 T cells is high, but is technically much more difficult and demanding in chronic viral infection, autoimmune disease and tumours.

3. Process the protein in vitro. Some of the cellular machinery that packages proteins for HLA display can be manipulated in a cell free environment. It may be possible to incubate PPI with this machinery and then examine the derived peptides for their ability to bind to HLA. This approach has not yet been tested convincingly and requires the additional step of testing the peptides for binding to the HLA.

Chang et al., (2003) *Tissue Antigens* 62: 408-417 discloses the ALWGPDPAAA peptide as one of 35 synthetic analogues of preproinsulin-derived peptides that are capable of being loaded in-vitro by soluble HLA-A2 molecules. This study also discloses 17 synthetic analogues of preproinsulin-derived peptides that are capable of being loaded in-vitro by soluble HLA-B8 and 17 synthetic analogues of preproinsulin-derived peptides that are capable of being loaded in-vitro by soluble HLA-B15 molecules. This study therefore identifies a large number of candidate peptides, some or all of which might conceivably be loaded by Class I HLAs in vivo. However, it is not possible to identify from this study which, if any, of the disclosed peptides are present in the peptide-MHC complexes used as targets by CD8 T cells in T1DM.

Rathmann et al., (2004) *Ann N.Y. Acad Sci* 1037: 22-25 discloses that a number of unspecified synthetic preproinsulin-derived peptides, including several peptides from within the signal sequence of preproinsulin are capable of eliciting a T cell response when pulsed on to the surface of PMBCs and CD8$^+$ T cells from two diabetic subjects. However, it is not possible to identify from this publication the identity of the individual peptides to which a T cell response was noted, or to identify the HLA molecule loading these pulsed peptides of the surface of the cells.

To summarise, neither of the above studies either individually or in combination, identify which preproinsulin-derived peptides a native preproinsulin containing cell presents in the context of a given MHC molecule such as HLA-A2. Without such information none of the preproinsulin peptide-HLA complexes disclosed in Chang et al., (2003) *Tissue Antigens* 62: 408-417 is identifiable as appropriate therapeutic targets.

BRIEF DESCRIPTION OF THE INVENTION

This invention makes available for the first time isolated preproinsulin-derived peptides of 8 or 9 amino acids, comprising the amino acid sequence WGPDPAA (SEQ ID NO: 1), isolated Class I peptide-HLA complexes presenting said peptides and isolated molecules having binding affinity for said peptides and/or said peptide-HLA complexes. Such compositions are useful in the treatment of type 1 diabetes mellitus (T1DM).

DETAILED DESCRIPTION OF THE INVENTION

The present invention provides isolated preproinsulin-derived peptides of 8 or 9 amino acids, comprising the amino acid sequence WGPDPAA (SEQ ID NO: 1). Hence, the peptides of the invention consist of the group:

ALWGPDPAA, (SEQ ID NO: 2)

LWGPDPAA, (SEQ ID NO: 3)

WGPDPAAA, (SEQ ID NO: 4)

WGPDPAAAF (SEQ ID NO: 5)
and

LWGPDPAAA. (SEQ ID NO: 6)

A specific embodiment of the current aspect is provided wherein the isolated preproinsulin peptide consists of the amino acid sequence WGPDPAAA (SEQ ID NO: 4).

As used herein the term preproinsulin is understood to comprise all of the amino acids encoded by a mammalian insulin gene. This includes additional "pro" and "signal" polypeptides which are lost from the mature form of mammalian insulin. FIG. 1 herein provides the amino acid sequence of human preproinsulin.

As used herein the term isolated peptide is understood to refer to a peptide which is provided in a substantially pure form, or as a purified or isolated preparation. For example, it may be provided in a form which is substantially free of other proteins.

The isolated preproinsulin peptide may comprise one, two or three altered amino acids relative to the corresponding native preproinsulin peptide. Such changes can be introduced by substituting, deleting or adding one, two, or three amino acids.

One aspect of the invention is provided by an isolated peptide major histocompatibility complex (peptide-MHC) wherein the MHC is a Human Leukocyte Antigen (HLA) class 1 molecule and the peptide is an isolated preproinsulin-derived peptide of 8 or 9 amino acids comprising the amino acid sequence WGPDPAA (SEQ ID NO: 1). In one embodiment of the current aspect the HLA molecule is HLA-A2. A further embodiment is provided by an isolated peptide-MHC complex of the invention wherein the peptide is WGPDPAAA (SEQ ID NO: 4). A related embodiment is provided by isolated peptide-MHC complexes of the invention associated with an imaging agent or therapeutic agent.

As used herein the term therapeutic agent is understood to refer to an agent capable of altering the symptoms and/or severity of type 1 diabetes mellitus. Preferably, the therapeutic agent will be a cytotoxic agent capable of killing those auto-reactive T cells that are involved in the progression of type 1 diabetes mellitus. More preferably, the therapeutic agent will be a cytotoxic agent capable of killing those auto-reactive T cells that recognise a Class I MHC molecule loaded with a preproinsulin-derived peptide of 8 or 9 amino acids comprising the amino acid sequence WGPDPAA (SEQ ID NO: 1). Most preferably, the therapeutic agent is selected from a *Pseudomonas* exotoxin or an anti-CD3 antibody.

Suitable therapeutic agents include, but are not limited to, *Pseudomonas* exotoxins and anti-CD3 antibodies. For example, anti-CD3 antibodies can be raised to any of the polypeptide chains from which this complex is formed (i.e. γ, δ, ε, ζ, and η CD3 chains). Antibodies which bind to the ε CD3 chain are the preferred anti-CD3 antibodies for use in the compositions and methods of the present invention. Suitable imaging agents include, but are not limited to, paramagnetic beads and $^{18}F$ which are used as imaging agents for nuclear magnetic resonance (NMR) and positron emission tomography (PET) scans respectively.

Also provided are nucleic acids coding for an isolated preproinsulin peptide of the invention. Related embodiments are provided by vectors comprising such nucleic acid and cells transformed with said vectors Another broad aspect of the invention is provided by an isolated molecule having specific binding affinity for a preproinsulin-derived peptide of 8 to 10 amino acids comprising the amino acid sequence WGPDPAA (SEQ ID NO: 1), or for a peptide-MHC complex wherein the MHC is an HLA Class I molecule and the peptide is a Preproinsulin-derived peptide of 8 to 10 amino acids comprising the amino acid sequence WGPDPAA (SEQ ID NO: 1). In this context, "a preproinsulin-derived peptide of 8 to 10 amino acids comprising the amino acid sequence WGPDPAA (SEQ ID NO: 1)" is a member of the group consisting of:

ALWGPDPAA, (SEQ ID NO: 2)

LWGPDPAA, (SEQ ID NO: 3)

WGPDPAAA, (SEQ ID NO: 4)

WGPDPAAAF, (SEQ ID NO: 5)

LWGPDPAAA, (SEQ ID NO: 6)

ALWGPDPAAA, (SEQ ID NO: 7)

LALWGPDPAA, (SEQ ID NO: 8)

LWGPDPAAAF (SEQ ID NO: 9)
and

WGPDPAAAFV. (SEQ ID NO: 10)

In one embodiment said molecules have specific binding affinity for a preproinsulin-derived peptide consisting of WGPDPAAA (SEQ ID NO: 4) or ALWGPDPAAA (SEQ ID NO: 7), or for a peptide-MHC complex wherein the MHC is an HLA Class I molecule and the peptide is a preproinsulin-derived peptide consisting of the amino acid sequence WGPDPAAA (SEQ ID NO: 4) or ALWGPDPAAA (SEQ ID NO: 7).

In one embodiment of the current aspect the said isolated molecule of the invention is an antibody.

Another embodiment of the current aspect is provided by T cell receptors (TCRs) or antibodies having specific binding affinity for a peptide-MHC complex wherein the MHC is an HLA Class I molecule and the peptide is a Preproinsulin-derived peptide of 8 to 10 amino acids, comprising the amino acid sequence WGPDPAA (SEQ ID NO: 1).

Specific embodiments of the current aspect are provided by TCRs or antibodies having specific binding affinity for a peptide-MHC complex wherein the MHC is an HLA Class I molecule and the peptide is a preproinsulin-derived peptide consisting of the amino acid sequence WGPDPAAA (SEQ ID NO: 4) or ALWGPDPAAA (SEQ ID NO: 7). Related aspects are provided wherein such isolated TCRs or antibodies of the invention are associated with an immunomodulatory agent, immunomodulatory cell type or imaging agent. Suitable immunomodulatory agents may be immunosuppressive agents; including but not limited to IL-10, IL13, IL-4 or functional variants or fragments of any of the foregoing. Suitable immunomodulatory cell types include, but are not limited to, autologous naturally arising regulatory T cells (nTregs). Suitable imaging agents include, but are not limited to, paramagnetic beads and $^{18}F$ which are used as imaging agents for Nuclear Magnetic Resonance (NMR) and Positron Emission Tomography (PET) scans respectively.

As used herein the term "functional variant" is understood to refer to analogues of the disclosed therapeutic agents which have the same therapeutic effect. For example, as is known to those skilled in the art, it may be possible to produce therapeutics that incorporate minor changes in the chemical structure or amino acid sequence thereof compared to those disclosed without altering the therapeutic effect of the agents. Such trivial variants are included in the scope of this invention.

Functional Antibody Fragments and Variants

Antibody fragments and variants/analogues which are suitable for use in the compositions and methods described herein include, but are not limited to, the following.

Antibody Fragments

As is known to those skilled in the art, it is possible to produce fragments of a given antibody which retain substantially the same binding characteristics as those of the parent antibody. The following provides details of such fragments:

Minibodies—These constructs consist of antibodies with a truncated Fc portion. As such they retain the complete binding domains of the antibody from which are derived.

Fab fragments—These comprise a single immunoglobulin light chain covalently-linked to part of an immunoglobulin heavy chain. As such, Fab fragments comprise a single antigen combining site. Fab fragments are defined by the portion of an IgG that can be liberated by treatment with papain. Such fragments are commonly produced via recombinant DNA techniques. (Reeves et al., (2000) *Lecture Notes on Immunology* (4th Edition) Published by Blackwell Science)

F(ab')$_2$ fragments—These comprise both antigen combining sites and the hinge region from a single antibody. F(ab')$_2$ fragments are defined by the portion of an IgG that can be liberated by treatment with pepsin. Such fragments are commonly produced via recombinant DNA techniques. (Reeves et al., (2000) *Lecture Notes on Immunology* (4th Edition) Published by Blackwell Science)

Fv fragments—These comprise an immunoglobulin variable heavy domain linked to an immunoglobulin variable light domain. A number of Fv designs have been produced. These include dsFvs, in which the association between the two domains is enhanced by an introduced disulfide bond. Alternatively, scFVs can be formed using a peptide linker to bind the two domains together as a single polypeptide. Fvs constructs containing a variable domain of a heavy or light immunoglobulin chain associated to the variable and constant domain of the corresponding immunoglobulin heavy or light chain have also been produced. FV have also been multimerised to form diabodies and triabodies (Maynard et al., (2000) *Annu Rev Biomed Eng* 2 339-376)

Nanobodies™—These constructs, marketed by Ablynx (Belgium), comprise synthetic single immunoglobulin variable heavy domain derived from a camelid (e.g. camel or llama) antibody.

Domain Antibodies—These constructs, marketed by Domantis (Belgium), comprise an affinity matured single immunoglobulin variable heavy domain or immunoglobulin variable light domain.

Antibody Variants and Analogues

The defining functional characteristic of antibodies in the context of the present invention is their ability to bind specifically to a target ligand. As is known to those skilled in the art it is possible to engineer such binding characteristics into a range of other proteins. Examples of antibody variants and analogues suitable for use in the compositions and methods of the present invention include, but are not limited to, the following.

Protein scaffold-based binding polypeptides—This family of binding constructs comprise mutated analogues of proteins which contain native binding loops. Examples include Affibodies, marketed by Affibody (Sweden), which are based on a three-helix motif derived from one of the IgG binding domains of *Staphylococcus aureus* Protein A. Another example is provided by Evibodies, marketed by EvoGenix (Australia) which are based on the extracellular domains of CTLA-4 into which domains similar to antibody binding loops are grafted. A final example, Cytokine Traps marketed by Regeneron Pharmaceuticals (US), graft cytokine receptor domains into antibody scaffolds. (Nygren et al., (2000) *Current Opinion in Structural biology* 7 463-469) provides a review of the uses of scaffolds for engineering novel binding sites in proteins. This review mentions the following proteins as sources of scaffolds: CP1 zinc finger, Tendamistat, Z domain (a protein A analogue), PST1, coiled coils, LACI-D1 and cytochrome $b_{562}$. Other protein scaffold studies have reported the use of fibronectin, green fluorescent protein (GFP) and ankyrin repeats.

In one broad aspect, the TCRs of the invention comprise both a TCR α chain variable domain and a TCR β chain variable domain In a further broad aspect, the TCRs of the invention are in the form of either single chain TCRs (scTCRs) or dimeric TCRs (dTCRs). Optionally, such TCRs may be provided as soluble TCRs.

In a further broad aspect, the TCRs of the invention are in the form of membrane embedded TCRs with functionally intact signalling properties, expressed by cells with immune modulatory properties such as nTregs.

In a specific embodiment, the soluble TCRs of the invention are in the form of either single chain TCRs (scTCRs) or dimeric TCRs (dTCRs) as described in WO 04/033685 and WO 03/020763 respectively. Examples 8 and 9 herein provide a detailed method for the production of soluble dimeric TCRs as described in WO 03/020763 which binds to the Class I peptide-MHC complexes of the invention.

According to one aspect, the present invention provides a T cell receptor (sTCR), which comprises (i) all or part of a TCR α chain, and (ii) all or part of a TCR β chain, wherein (i) and (ii) are linked by a disulphide bond which is not present in native αβ TCRs.

According to a further aspect, the present invention provides a T cell receptor, which comprises (i) all or part of a TCR α chain, except the transmembrane domain thereof, and (ii) all or part of a TCR β chain, except the transmembrane domain thereof, wherein (i) and (ii) each comprise a functional variable domain and at least a part of the constant domain of the TCR chain, and are linked by a disulphide bond which is not present in native αβ TCRs.

According to a further aspect, the present invention provides a T cell receptor, which comprises (i) a TCR α chain comprising a variable α domain, a constant α domain and a first dimerisation motif attached to the C-terminus of the constant α domain, and (ii) a TCR β chain comprising a variable β domain, a constant β domain and a first dimerisation motif attached to the C-terminus of the constant 13 domain, wherein the first and second dimerisation motifs easily interact to form a covalent bond between an amino acid in the first dimerisation motif and an amino acid in the second dimerisation motif linking the TCR α chain and TCR β chain together.

In one specific embodiment of the invention such αβ TCRs comprise all of the extracellular constant Ig domain of the TCR chain.

In another specific embodiment of the invention such αβ TCRs comprise all of the extracellular domain of the TCR chain.

A suitable dTCR form of the TCRs of the present invention comprises a first polypeptide wherein a sequence corresponding to a TCR α chain variable region sequence is fused to the N terminus of a sequence corresponding to a TCR α chain constant domain extracellular sequence, and a second polypeptide wherein a sequence corresponding to a TCR β chain variable region sequence is fused to the N terminus of a sequence corresponding to a TCR β chain constant domain extracellular sequence, the first and second polypeptides being linked by a disulfide bond which has no equivalent in native αβ T cell receptors.

The first polypeptide may comprise a TCR α chain variable region sequence fused to the N terminus of a sequence corresponding to a TCR α chain constant domain extracellular sequence, and a second polypeptide wherein a sequence corresponding to a TCR β chain variable region sequence is fused to the N terminus a sequence corresponding to a TCR β chain constant domain extracellular sequence, the first and second polypeptides being linked by a disulfide bond between cysteine residues substituted for Thr 48 of exon 1 of TRAC*01 and Ser 57 of exon 1 of TRBC1*01 or TRBC2*01 or the non-human equivalent thereof. ("TRAC" etc. nomenclature herein as per T cell receptor Factsbook, (2001) LeFranc and LeFranc, Academic Press, ISBN 0-12-441352-8)

The dTCR or scTCR form of the TCRs of the invention may have amino acid sequences corresponding to human αβ TCR extracellular constant and variable domain sequences, and a disulfide bond may link amino acid residues of the said constant domain sequences, which disulfide bond has no equivalent in native TCRs. The disulfide bond is between cysteine residues corresponding to amino acid residues whose β carbon atoms are less than 0.6 nm apart in native TCRs, for example between cysteine residues substituted for Thr 48 of exon 1 of TRAC*01 and Ser 57 of exon 1 of TRBC1*01 or TRBC2*01 or the non-human equivalent thereof. Other sites where cysteines can be introduced to form the disulfide bond are the following residues in exon 1 of TRAC*01 for the TCR α chain and TRBC1*01 or TRBC2*01 for the TCR β chain:

| TCR α chain | TCR β chain | Native β carbon separation (nm) |
| --- | --- | --- |
| Thr 45 | Ser 77 | 0.533 |
| Tyr 10 | Ser 17 | 0.359 |
| Thr 45 | Asp 59 | 0.560 |
| Ser 15 | Glu 15 | 0.59 |

A preferred embodiment is provided by an isolated TCR of the invention which is a dTCR comprising
a first polypeptide wherein a sequence corresponding to a TCR α chain variable region sequence is fused to the N terminus of a sequence corresponding to a TCR α chain constant domain extracellular sequence, and
a second polypeptide wherein a sequence corresponding to a TCR β chain variable region sequence is fused to the N terminus of a sequence corresponding to a TCR β chain constant domain extracellular sequence,
the first and second polypeptides being linked by a disulfide bond between cysteine residues substituted for Thr 48 of exon 1 of TRAC*01 and Ser 57 of exon 1 of TRBC1*01 or TRBC2*01 or the non-human equivalent thereof.

In addition to the non-native disulfide bond referred to above, the dTCR or scTCR form of the TCRs of the invention may include a disulfide bond between residues corresponding to those linked by a disulfide bond in native TCRs.

The dTCR or scTCR form of the TCRs of the invention preferably does not contain a sequence corresponding to transmembrane or cytoplasmic sequences of native TCRs.

In one aspect of the invention this covalent disulfide bond links a residue of the immunoglobulin region of the constant domain of the α chain to a residue of the immunoglobulin region of the constant domain of the β chain.

Another aspect of the invention is provided wherein, in the αβ, TCR, an interchain disulfide bond present in native TCRs is absent. A specific embodiment of this aspect is provided wherein, in the soluble αβ TCR, native α and β TCR chains are truncated at the C-terminus such that the cysteine residues which form the native interchain disulfide bond are excluded. In an alternative embodiment the cysteine residues which form the native interchain disulfide bond are substituted by another residue. In another specific embodiment, the cysteine residues which form the native interchain disulfide bond are substituted by serine or alanine.

ImmunoGeneTics (IMGT) nomenclature as described in (LeFranc et al, (2001) The T cell receptor Factsbook, Academic Press) will be used throughout this application to denote the position of particular amino acid residues in TCR chains.

A further aspect of the invention is provided wherein the soluble αβ TCR comprises all or part of a TCR α chain except the transmembrane domain thereof and all or part of a TCR β chain except the transmembrane domain thereof, wherein each TCR chain comprises the functional variable domain of a first TCR fused to all or part of the constant domain of a second TCR, the first and second TCRs being from the same species.

As used herein the term "TCR variable region" is understood to encompass all amino acids of a given TCR which are not included within the constant domain as encoded by the TRAC gene for TCR α chains and either the TRBC1 or TRBC2 genes for TCR β chains. (T cell receptor Factsbook, (2001) LeFranc and LeFranc, Academic Press, ISBN 0-12-441352-8).

As used herein the term "TCR variable domain" is understood to encompass all amino acids of a given TCR which are encoded by a TRAV gene for TCR α chains and a TRBV gene for TCR β chains. (T cell receptor Factsbook, (2001) LeFranc and LeFranc, Academic Press, ISBN 0-12-441352-8)

Additional aspects are provided wherein the isolated soluble TCRs of the invention further comprises a detectable label or an immuno-inhibitory agent. Suitable inhibitory agents include, but are not limited to IL-10, IL13, IL-4 or functional variants or fragments of any of the foregoing.

PEGylated TCR Monomers

In one particular embodiment a TCR of the invention is associated with at least one polyalkylene glycol chain. This association may be created in any of a number of ways known to those skilled in the art. In a preferred embodiment the polyalkylene chain(s) is/are covalently linked to the TCR. In a further embodiment the polyethylene glycol chains of the present aspect of the invention comprise at least two polyethylene repeating units.

Multivalent TCR Complexes

One aspect of the invention provides a multivalent TCR complex comprising at least two TCRs of the invention. In one embodiment of this aspect, at least two TCR molecules are linked via linker moieties to form multivalent complexes. Preferably, the complexes are water soluble, so the linker moiety should be selected accordingly. One embodiment of the present aspect is provided by multivalent TCR complexes linked by a non-peptidic polymer chain or a peptidic linker sequence. Furthermore, it is preferable that the linker moiety should be capable of attachment to defined positions on the TCR molecules, so that the structural diversity of the complexes formed is minimised. One embodiment of the present aspect is provided by a TCR complex of the invention wherein the polymer chain or peptidic linker sequence extends between amino acid residues of each TCR which are not located in a variable region sequence of the TCR.

Since the complexes of the invention may be for use in medicine, the linker moieties should be chosen with due regard to their, pharmaceutical suitability, for example their immunogenicity.

Examples of linker moieties which fulfil the above desirable criteria are known in the art, for example the art of linking antibody fragments.

There are two classes of linker that are preferred for use in the production of multivalent TCR molecules of the present invention. A TCR complex of the invention in which the TCRs are linked by a polyalkylene glycol chain provides one embodiment of the present aspect.

The first are hydrophilic polymers such as polyalkylene glycols. The most commonly used of this class are based on polyethylene glycol or PEG, the structure of which is shown below.

HOCH$_2$CH$_2$O (CH$_2$CH$_2$O)$_n$—CH$_2$CH$_2$OH

Wherein n is greater than two. However, others are based on other suitable, optionally substituted, polyalkylene glycols include polypropylene glycol, and copolymers of ethylene glycol and propylene glycol.

The polymer used can have a linear or branched conformation. Branched PEG molecules, or derivatives thereof, can be induced by the addition of branching moieties including glycerol and glycerol oligomers, pentaerythritol, sorbitol and lysine.

Usually, the polymer will have a chemically reactive group or groups in its structure, for example at one or both termini, and/or on branches from the backbone, to enable the polymer to link to target sites in the TCR. This chemically reactive group or groups may be attached directly to the hydrophilic polymer, or there may be a spacer group/moiety between the hydrophilic polymer and the reactive chemistry as shown below:

Reactive chemistry-Hydrophilic polymer-Reactive chemistry

Reactive chemistry-Spacer-Hydrophilic polymer-Spacer-Reactive chemistry

The spacer used in the formation of constructs of the type outlined above may be any organic moiety that is a non-reactive, chemically stable chain. Such spacers include, by are not limited to the following:

—(CH$_2$)$_n$— wherein n=2 to 5

A TCR complex of the invention in which a divalent alkylene spacer radical is located between the polyalkylene glycol chain and its point of attachment to a TCR of the complex provides a further embodiment of the present aspect.

A TCR complex of the invention in which the polyalkylene glycol chain comprises at least two polyethylene glycol repeating units provides a further embodiment of the present aspect.

Peptidic linkers are the other class of TCR linkers. These linkers are comprised of chains of amino acids, and function to produce simple linkers or multimerisation domains onto which TCR molecules can be attached. The biotin/streptavidin system has previously been used to produce TCR tetramers (see WO/99/60119) for in-vitro binding studies. However, streptavidin is a microbially-derived polypeptide and as such not ideally suited to use in a therapeutic.

A TCR complex of the invention in which the TCRs are linked by a peptidic linker derived from a human multimerisation domain provides a further embodiment of the present aspect.

A multivalent TCR complex of the invention comprising at least two TCRs provides a final embodiment of this aspect.

WO 2004/050705 provides details of appropriate linker moieties for use in multivalent TCR complexes of the invention.

One aspect is provided by the use of an isolated preproinsulin-derived peptide of 8 to 10 amino acids comprising the amino acid sequence WGPDPAA (SEQ ID NO: 1), or a peptide-MHC complex wherein the MHC is an HLA Class I molecule and the peptide is a Preproinsulin-derived peptide of 8 to 10 amino acids comprising the amino acid sequence WGPDPAA (SEQ ID NO: 1) for the identification of a molecule have specific binding affinity for said peptides or peptide-MHC complexes.

A further aspect of the invention is provided by a cell transfected with genetic material encoding an HLA class I molecule and a preproinsulin-derived peptide of 8 to 10 amino acids comprising the amino acid sequence WGPDPAA (SEQ ID NO: 1). Said cell may be a K562 cell.

Examples 1 to 4 herein provide details of the use of K562 cells transfected with DNA encoding human preproinsulin and HLA-A2 for the identification of preproinsulin-derived peptides which are loaded by HLA-A2.

One aspect of the invention is provided by an isolated preproinsulin-derived peptide of 8 to 10 amino acids comprising the amino acid sequence WGPDPAA (SEQ ID NO: 1) for use in therapy. Specific embodiments of the present aspect are provided by preproinsulin-derived peptides consisting of the amino acid sequence WGPDPAAA (SEQ ID NO: 4) or ALWGPDPAAA (SEQ ID NO: 7) for use in therapy.

An additional aspect of the invention is provided by an isolated peptide-MHC complex wherein the MHC is an HLA Class I molecule and the peptide is a preproinsulin-derived peptide of 8 to 10 amino acids comprising the amino acid sequence WGPDPAA (SEQ ID NO: 1) for use in therapy. Specific embodiments for the present aspect are provided wherein the MHC is an HLA Class I molecule and the peptide is a preproinsulin-derived peptide of 8 to 10 amino acids consisting of the amino acid sequence WGPDPAAA (SEQ ID NO: 4) or ALWGPDPAAA (SEQ ID NO: 7) for use in therapy.

A further aspect of the invention is provided by an isolated nucleic acid molecule coding for a preproinsulin-derived peptide of 8 to 10 amino acids comprising the amino acid sequence WGPDPAA (SEQ ID NO: 1) for use in therapy.

Another aspect of the invention is provided by an isolated molecule having specific binding affinity for a preproinsulin-derived peptide of 8 to 10 amino acids comprising the amino acid sequence WGPDPAA (SEQ ID NO: 1), or for a peptide-MHC complex wherein the MHC is an HLA Class 1 molecule and the peptide is a preproinsulin-derived peptide of 8 to 10 amino acids comprising the amino acid sequence WGPDPAA (SEQ ID NO: 1) for use in therapy.

A further aspect for the invention is provided by a pharmaceutical composition adapted for parenteral administration comprising a preproinsulin-derived peptide of 8 to 10 amino acids comprising the amino acid sequence WGPDPAA (SEQ ID NO: 1), or a nucleic acid coding for a preproinsulin-derived peptide of 8 to 10 amino acids comprising the amino acid sequence WGPDPAA (SEQ ID NO: 1), or a peptide-MHC complex wherein the MHC is an HLA Class 1 molecule and the peptide is a preproinsulin-derived peptide of 8 to 10 amino acids comprising the amino acid sequence WGPDPAA (SEQ ID NO: 1) or an isolated molecule having specific binding affinity such peptides and/or for such peptide-MHC complexes and a pharmaceutically acceptable carrier. Related embodiments are provided by a pharmaceutical composition adapted for parenteral administration comprising these peptide-MHC complexes, or isolated molecules having specific binding affinity such peptides and/or for such peptide-MHC complexes associated with a therapeutic or immunomodulatory agent and a pharmaceutically acceptable carrier.

A further aspect of the invention provides the pharmaceutical composition of the invention for use in therapy, especially in the treatment of type 1 diabetes mellitus.

A further aspect of the invention is provided by a method of treating type 1 diabetes mellitus comprising administering a therapeutic amount of a preproinsulin-derived peptide of 8 to 10 amino acids comprising the amino acid sequence WGPDPAA (SEQ ID NO: 1), or a nucleic acid coding for a preproinsulin-derived peptide of 8 to 10 amino acids comprising the amino acid sequence WGPDPAA (SEQ ID NO: 1), or a peptide-MHC complex wherein the MHC is an HLA Class 1 molecule and the peptide is a preproinsulin-derived peptide of 8 to 10 amino acids comprising the amino acid sequence WGPDPAA (SEQ ID NO: 1) or an isolated molecule having specific binding affinity such peptides and/or for such peptide-MHC complexes to a subject in need thereof. Related embodiments are provided by a method of treating type 1 diabetes mellitus comprising administering a therapeutic amount of these peptide-MHC complexes, or isolated molecules having specific binding affinity such peptides and/or for such peptide-MHC complexes associated with a therapeutic or immunomodulatory agent to a subject in need thereof.

A further aspect of the invention is provided by the use of a preproinsulin-derived peptide of 8 to 10 amino acids comprising the amino acid sequence WGPDPAA (SEQ ID NO: 1), or a nucleic acid coding for a preproinsulin-derived peptide of 8 to 10 amino acids comprising the amino acid sequence WGPDPAA (SEQ ID NO: 1), or a peptide-MHC complex wherein the MHC is an HLA Class 1 molecule and the peptide is a Preproinsulin-derived peptide of 8 to 10 amino acids comprising the amino acid sequence WGPDPAA (SEQ ID NO: 1) or an isolated molecule having specific binding affinity such peptides and/or for such peptide-MHC complexes in the treatment of type 1 diabetes mellitus or in the preparation of a medicament for the treatment of type 1 diabetes mellitus, said medicament being adapted for administration by a subcutaneous, intradermal or intramuscular route. Related embodiments are provided by the use of these peptide-MHC complexes, or isolated molecules having specific binding affinity such peptides and/or for such peptide-MHC complexes associated with a therapeutic or immunomodulatory agent in the treatment of type 1 diabetes mellitus or in the preparation of a medicament for the treatment of type 1 diabetes mellitus.

The invention also provides a method of diagnosing type 1 diabetes mellitus or monitoring the severity of type 1 diabetes mellitus, comprising the use of a molecule having specific binding affinity for a peptide-MHC complex wherein the MHC is an HLA Class 1 molecule and the peptide is a preproinsulin-derived peptide of 8 to 10 amino acids comprising the amino acid sequence WGPDPAA (SEQ ID NO: 1) to quantify the level of cognate pMHC molecules in a test subject, wherein a decreased level of said pMHC molecules compared to that present in a healthy individual, or the same test subject at an earlier time-point, indicates the presence, or severity of type 1 diabetes mellitus. In certain embodiments of the present aspect of the invention this method may be carried out in-vivo or in-vitro on a sample taken from the test subject.

A further aspect of the invention is provided by an in-vitro method of diagnosing type 1 diabetes mellitus or monitoring the severity of type 1 diabetes mellitus, said method comprising contacting peptide-MHC molecules of the invention with a sample obtained from a subject under conditions suitable for allowing auto-reactive T cells in the test sample to bind to said peptide-MHC molecules. In one embodiment of the present aspect the test sample is contacted with said peptide-MHC molecules in a suitable immunoassay, for example a cytokine enzyme-linked immunospot (ELISPOT) assay. In another embodiment of the present aspect the test sample is contacted with the peptides of the invention under condition suitable for allowing said peptides to be presented by the MHC molecules on the surface of the cells within the test sample. The auto-reactive T cell response obtained can be quantified by a number of cell activation assays, including but not limited to, cytokine release assays, intracellular cytokine secretion assays, detection of activation of signal transduction pathways downstream of the TCR and microarray detection of mRNA for species of proteins that indicate a T cell response such as cytokine mRNA.

A final aspect of the invention is provided by in-vitro method of diagnosing type 1 diabetes mellitus or monitoring the severity of type 1 diabetes mellitus, comprising the use of peptide-MHC complexes of the invention associated with an imaging agent according to quantify auto-reactive T cells capable of specifically binding to said peptide-MHC complexes in a sample obtained from a test subject wherein an increased level of said T cells compared to that present in a healthy individual, or the same test subject at an earlier time-point, indicates the presence, or severity, of type 1 diabetes mellitus.

Additional Aspects

The invention provides a method for delivering a molecule having specific binding affinity for a peptide-MHC complex wherein the MHC is a HLA Class I molecule and the peptide is a preproinsulin-derived peptide of 8 to 10 amino acids comprising the amino acid sequence WGPDPAA (SEQ ID NO: 1) to a target cell. TCRs and antibodies are examples of such molecules having specific binding affinity for said peptide-MHC complexes. It is believed that such specific binding molecules will be preferentially delivered to the β islet cells of the pancreas which are the target cells for attack by the "misdirected" T cells which, at least in part, cause type I diabetes. Without wishing to be bound by theory the targeted delivery of these specific binding molecules facilitates two means of counter-acting the T cell-mediated attack of these β islet cells. Firstly, the specific binding molecules may directly block the "misdirected" T cells from binding to the β islet cells by occupying the peptide-MHC molecules on the β islet cells to which these T cells would otherwise bind. Secondly, the specific binding molecules of the present invention can be used to deliver immunomodulatory agents to the location of the β islet cells. An immunomodulatory agent could be delivered such that it would exercise its effect locally but not only on the β islet cell to which it binds.

Thus, one particular strategy envisages immunomodulatory molecules linked to the specific binding molecules according to the invention specific for type 1 diabetes mellitus-related peptide-MHC molecules. For example, a β islet cell-specific soluble TCR could be used to deliver an immunosuppressive agent, such as IL-10, IL-4 or IL-13 or a functional variant or fragment of any of the foregoing to the β islet cells of a patient suffering from diabetes.

As used herein the term immunomodulatory agent is understood to refer to an agent capable of altering one or more immune response to an antigen. Preferably, the immune response to be altered is the inflammatory response associated with type 1 diabetes mellitus. More preferably, the immune response to be altered is a T cell-mediated immune response to an antigen which forms part of the inflammatory response associated with type 1 diabetes mellitus. It is further preferred if the immune response to be altered is an auto-reactive T cell-mediated response to an antigen which forms part of the inflammatory response associated with type 1 diabetes mellitus. Most preferably the immune response to be altered is a CD8+ T cell-mediated auto-reactive response to an antigen which forms part of the inflammatory response associated with type 1 diabetes mellitus. Preferably, the antigen is a Class I MHC molecule loaded with a preproinsulin-derived peptide of 8 or 9 amino acids comprising the amino acid sequence WGPDPAA (SEQ ID NO: 1). More preferably, the antigen is a HLA-A2 molecule loaded with a preproinsulin-derived peptide of 8 or 9 amino acids comprising the amino acid sequence WGPDPAA (SEQ ID NO: 1).

As used herein the term immunosuppressive agent is understood to refer to an immunomodulatory agent capable of reducing or abolishing one or more immune response to an antigen. Preferably, the immune response to be reduced or abolished is the inflammatory response associated with type 1 diabetes mellitus. More preferably, the immune response to be reduced or abolished is a T cell-mediated immune response to an antigen which forms part of the inflammatory response associated with type 1 diabetes mellitus. It is further preferred if the immune response to be reduced or abolished is an auto-reactive T cell-mediated response to an antigen which forms part of the inflammatory response associated with type 1 diabetes mellitus. Most preferably the immune response to be reduced or abolished is a CD8+ T cell-mediated auto-reactive response to an antigen which forms part of the inflammatory response associated with type 1 diabetes mellitus. Preferably, the antigen is a class I MHC molecule loaded with a preproinsulin-derived peptide of 8 or 9 amino acids comprising the amino acid sequence WGPDPAA (SEQ ID NO: 1). More preferably, the antigen is a HLA-A2 molecule loaded with a preproinsulin-derived peptide of 8 or 9 amino acids comprising the amino acid sequence WGPDPAA (SEQ ID NO: 1).

As used herein the term "functional variant" is understood to refer to analogues of the disclosed immunomodulatory agents which have the same therapeutic effect. For example, as is known to those skilled in the art, it may be possible to produce immunomodulatory agents that incorporate minor changes in the chemical structure or amino acid sequence thereof compared to those disclosed without altering the therapeutic effect of the agents. Such trivial variants are included in the scope of this invention.

Therapeutic peptides, peptide-MHC molecules and specific binding molecules in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example parenteral, transdermal or via inhalation, preferably a parenteral (including subcutaneous, intramuscular, or, most preferably intravenous) route. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. and a physician will ultimately determine appropriate dosages to be used.

A soluble peptide, peptide-MHC complex, αβ TCR, multivalent TCR complex or antibody of the present invention may be provided in substantially pure form, or as a purified or isolated preparation. For example, it may be provided in a form which is substantially free of other proteins.

Gene cloning techniques may be used to provide a soluble αβ TCR or peptide-MHC complex of the invention, preferably in substantially pure form. These techniques are disclosed, for example, in J. Sambrook et al *Molecular Cloning* 2nd Edition, Cold Spring Harbor Laboratory Press (1989). Thus, in a further aspect, the present invention provides a nucleic acid molecule comprising a sequence encoding a chain of the soluble TCR or a peptide-MHC complex of the present invention, or a sequence complementary thereto. Nucleic acid molecules encoding a chain of a soluble TCR of the invention may be obtained by making appropriate mutations (by insertion, deletion or substitution) to TCR-encoding nucleic acid isolated from T-cell clones or by de-novo synthesis of published αβ TCR DNA sequences.

The nucleic acid molecules of the invention may be in isolated or recombinant form. Such nucleic acid molecules may be incorporated into a vector and the vector may be incorporated into a host cell. Such vectors and suitable hosts form yet further aspects of the present invention.

Also provided is a method for obtaining a soluble TCR or β TCR chain, or peptide-MHC complex of the invention, which method comprises incubating such a host cell under conditions causing expression of the TCR chain or peptide-MHC complex and then purifying the polypeptide.

The soluble αβ TCRs or peptide-MHC complexes of the present invention may obtained by expression in a bacterium such as *E. coli* as inclusion bodies, and subsequent refolding in vitro.

Refolding of the soluble αβ TCR chains or peptide-MHC complexes may take place in vitro under suitable refolding conditions. In a particular embodiment, a TCR or peptide-MHC complex with correct conformation is achieved by refolding solubilised TCR chains or the peptide-MHC in a refolding buffer comprising a solubilising agent, for example guanidine. Advantageously, the guanidine may be present at a concentration of at least 0.1M or at least 1M or at least 2.5M, or about 6M. An alternative solubilising agent which may be used is urea, at a concentration of between 0.1M and 8M, preferably at least 1M or at least 2.5M. Prior to refolding, a reducing agent is preferably employed to ensure complete reduction of cysteine residues.

As is known to those skilled in the art the refolding methods utilised be varied in order to optimise the yield of refolded protein obtained. For example, further denaturing agents such as DTT and guanidine may be used as necessary. Alternatively or additionally, different denaturants and reducing agents may be used prior to the refolding step (e.g. urea, β-mercaptoethanol). Alternatively or additionally, redox couples may be used during refolding, such as a cystamine/cysteamine redox couple, DTT or β-mercaptoethanol/atmospheric oxygen, and cysteine in reduced and oxidised forms.

Folding efficiency may also be increased by the addition of certain other protein components, for example chaperone proteins, to the refolding mixture. Improved refolding has been achieved by passing protein through columns with immobilised mini-chaperones (Altamirano, et al. (1999). *Nature Biotechnology* 17: 187-191; Altamirano, et al. (1997). *Proc Natl Acad Sci USA* 94(8): 3576-8).

Alternatively, soluble TCRs or peptide-MHC complexes of the present invention may obtained by expression in a eukaryotic cell system, such as insect cells.

Purification of the soluble TCR or peptide-MHC complex may be achieved by many different means. Alternative modes of ion exchange may be employed or other modes of protein purification may be used such as gel filtration chromatography or affinity chromatography.

Gene cloning techniques may also be used to provide a membrane bound αβ TCR or peptide-MHC complex of the invention, using, for example, a viral vector. Such techniques are well known in the art. In particular, the membrane bound TCR or peptide-MHC complex may be expressed on a cell having immune modulatory or immune regulatory properties, such as nTregs.

Preferred features of each aspect of the invention are as for each of the other aspects *mutatis mutandis*. The prior art documents mentioned herein are incorporated to the fullest extent permitted by law.

EXAMPLES

The invention is further described in the following examples, which do not limit the scope of the invention in any way.

Reference is made in the following to the accompanying drawings in which:

FIG. 1 is the amino acid sequence of human pre-proinsulin. The pre sequence is indicated by shading, the pro sequence (C peptide) is indicated by unaltered text, the B chain is indicated by unlining and the A chain is indicated by itallic text.

Figure 3:
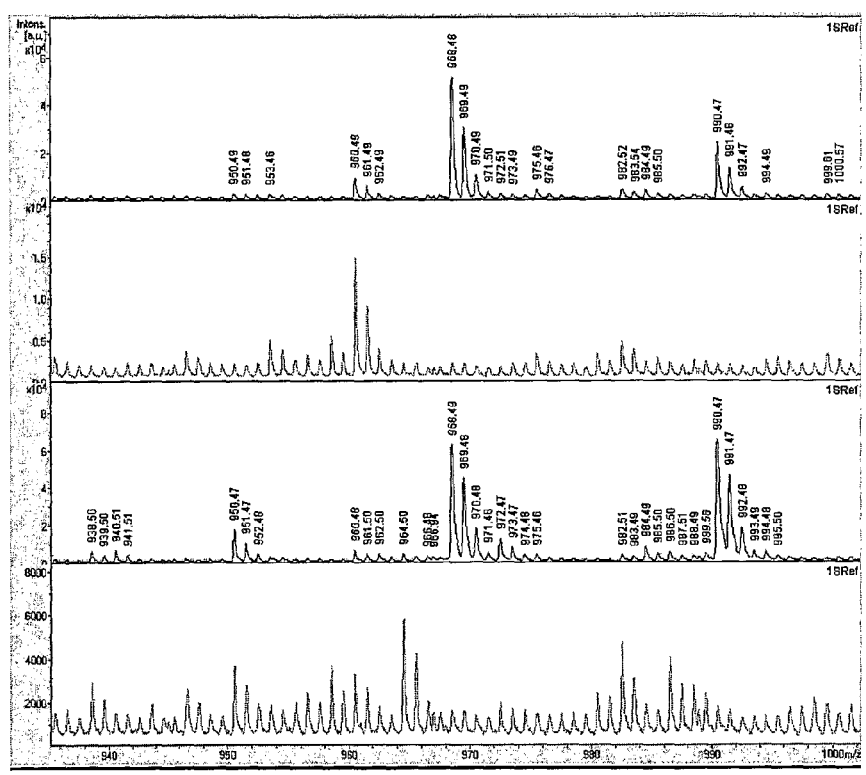

FIG. 3 is a mass spectrum showing the unique mass at m/z 968.48. A selection of the entire m/z spectrum analysed for two adjacent peptide fractions is shown. Traces from peptides derived from K562-A2-PPI are shown and reveal a unique mass at 968.48 not found in the control fractions from corresponding K562-A2 control fractions.

Figure 4:
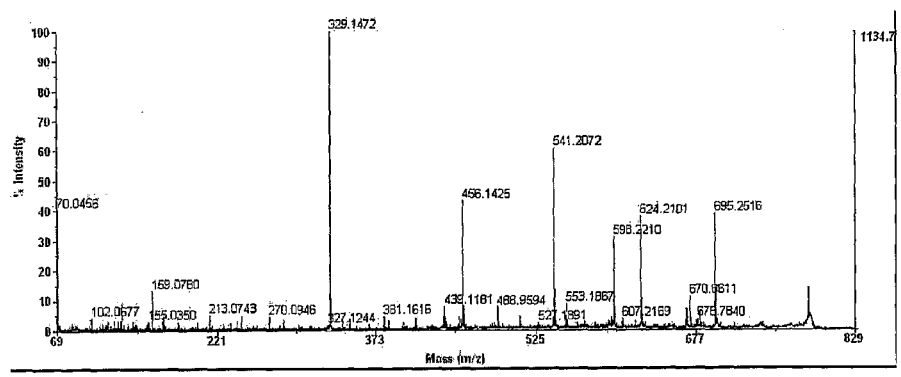

FIG. 4 shows MS/MS Fragmentation of m/z 784.37. The unique mass at m/z 784.37 in fraction 55 from K562-A2 PPI was fragmented by CID resulting in a characteristic pattern of peptide fragments.

Figure 5:
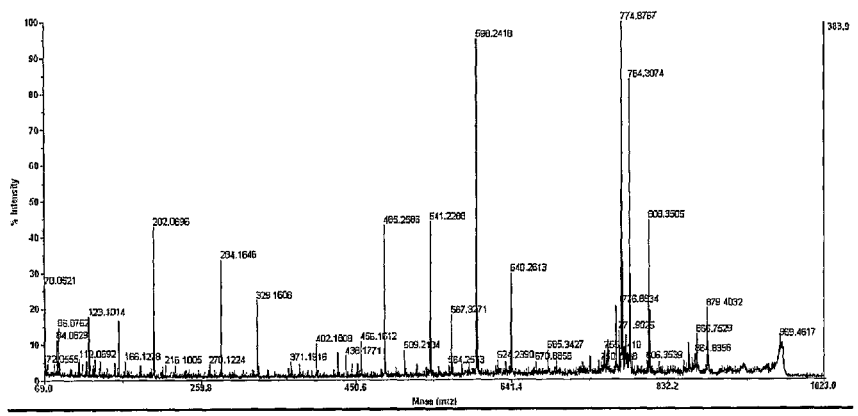

FIG. 5 shows MS/MS Fragmentation of m/z 968.48. The unique mass at m/z 968.48 from fraction 65 of K562-A2 PPI, shown as fragmented by CID.

Figure 6:
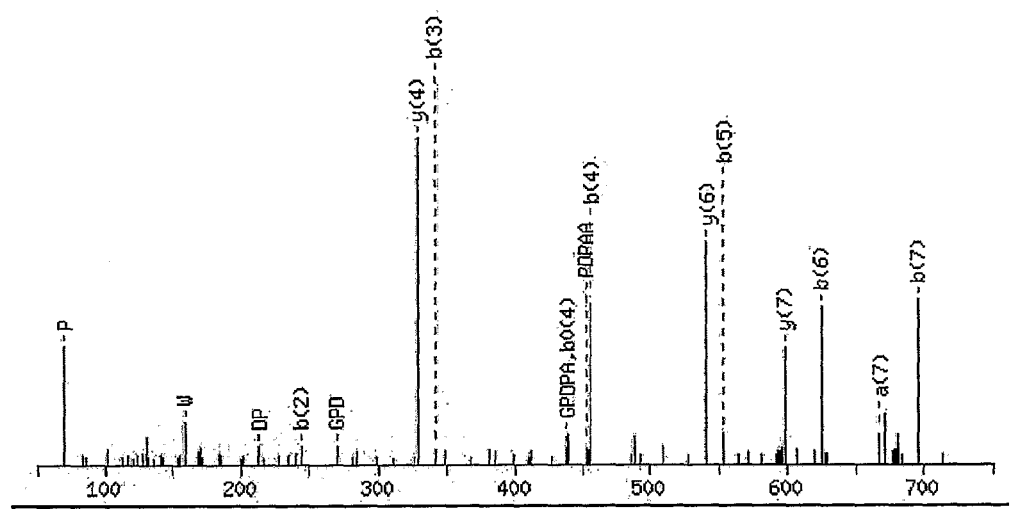

FIG. 6 shows Mascot analysis of m/z 784.37 MS/MS fragmentation pattern. Top: Ions are matched by Mascot to the most likely candidate, protein sequence (here PPI) based on relative abundance (height of red bars). The x axis represents the m/z spectrum, and ions matched to the fragments of the PPI-derived sequence $PPI_{17-24}$ (WGPDPAAA (SEQ ID NO: 4)) are indicated. Bottom: Ions from the WGPDPAAA (SEQ ID NO: 4) sequence which were amongst those produced by MS/MS fragmentation are shown in red. The distinct pattern notably of y and b ions confirms this as the identity of the m/z 784.37 unique mass.

Figure 7:
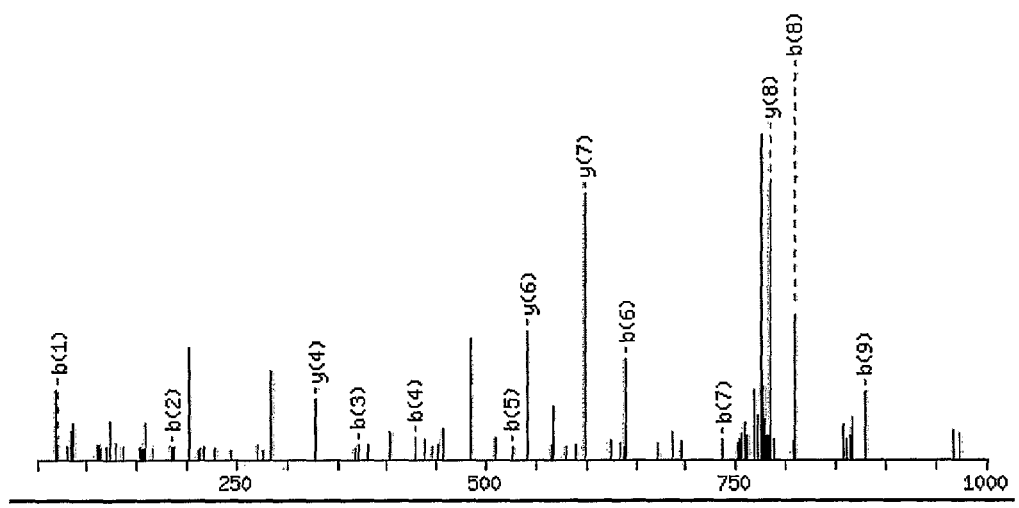

FIG. 7 shows Mascot analysis of m/z 968.48 MS/MS fragmentation pattern

Figure 8A:
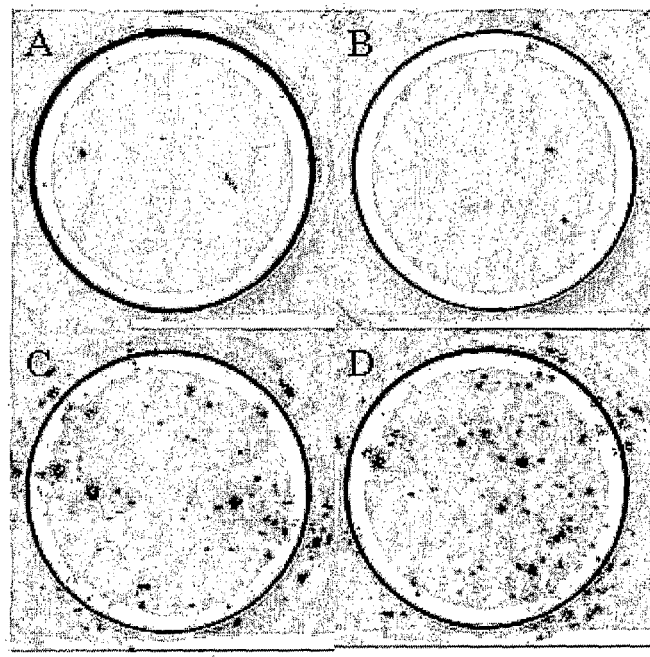

FIG. 8*a* is an example of cytokine ELISPOT detection of CD8 cells from a type 1 diabetic patient responding to $PPI_{15-24}$ [C], $PPI_{17-24}$ [D] compared with controls (no peptide A & B)

Figure 8B:
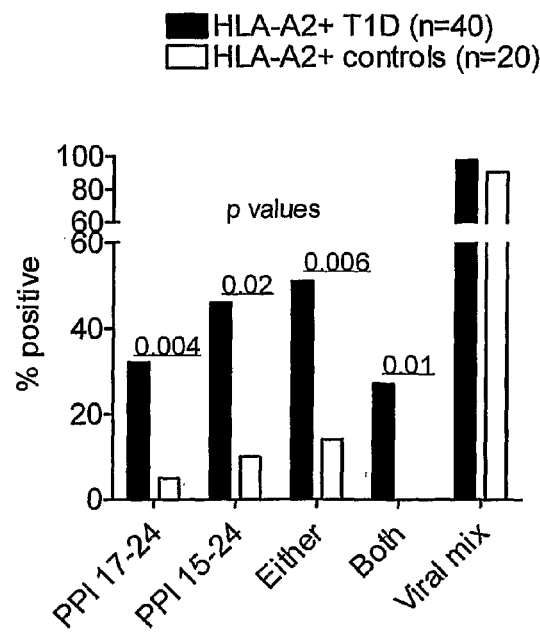

FIG. 8*b* shows the percentage of HLA-A2+ type 1 diabetic patients showing CD8 T cell reactivity to PPI peptides by interferon-gamma ELISPOT analysis.

Figure 9:
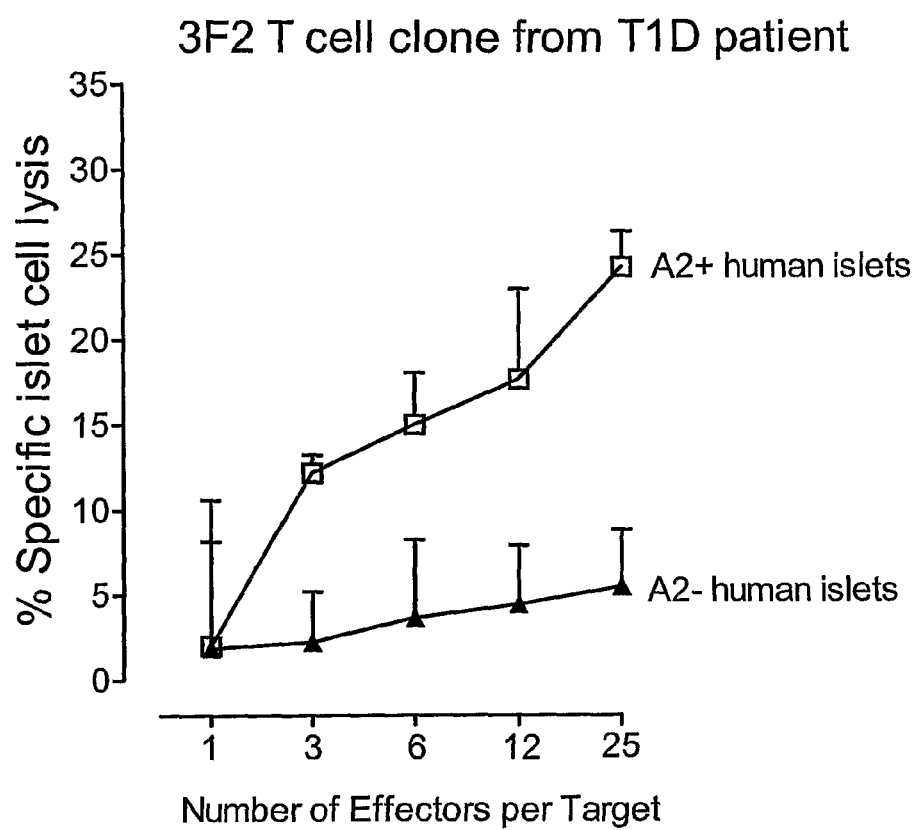

FIG. 9 shows that a CD8+ T cell clone designated 3F2, which is specific for a PPI peptide containing the sequence WGPDPAA (SEQ ID NO: 1) and was isolated from one of the T1DM patients studied in FIG. 8*b*, is able to respond to human beta cells presenting the same or similar sequence by specific killing. This confirms that the peptide species identified by elution from the K562-A2 PPI cell line is presented naturally by human islet cells.

Figure 14:
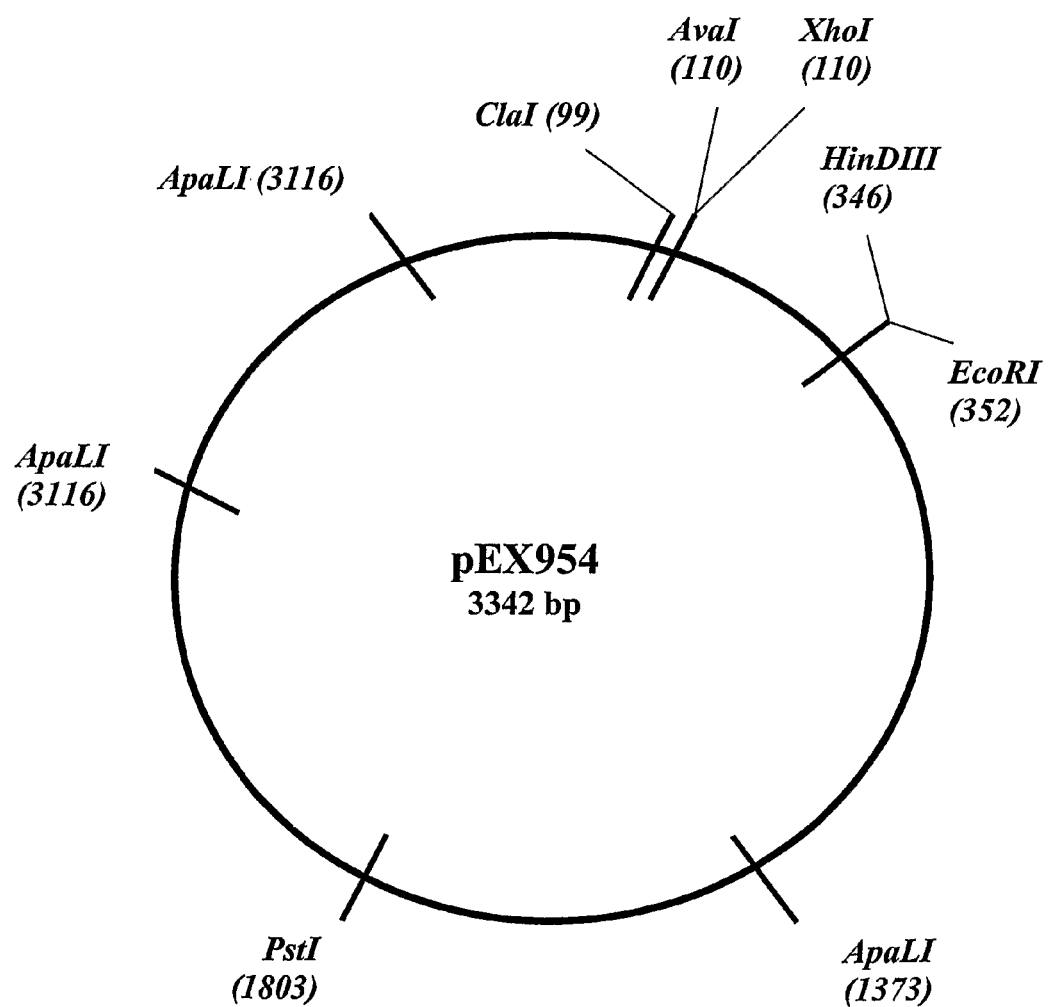
Figure 15:
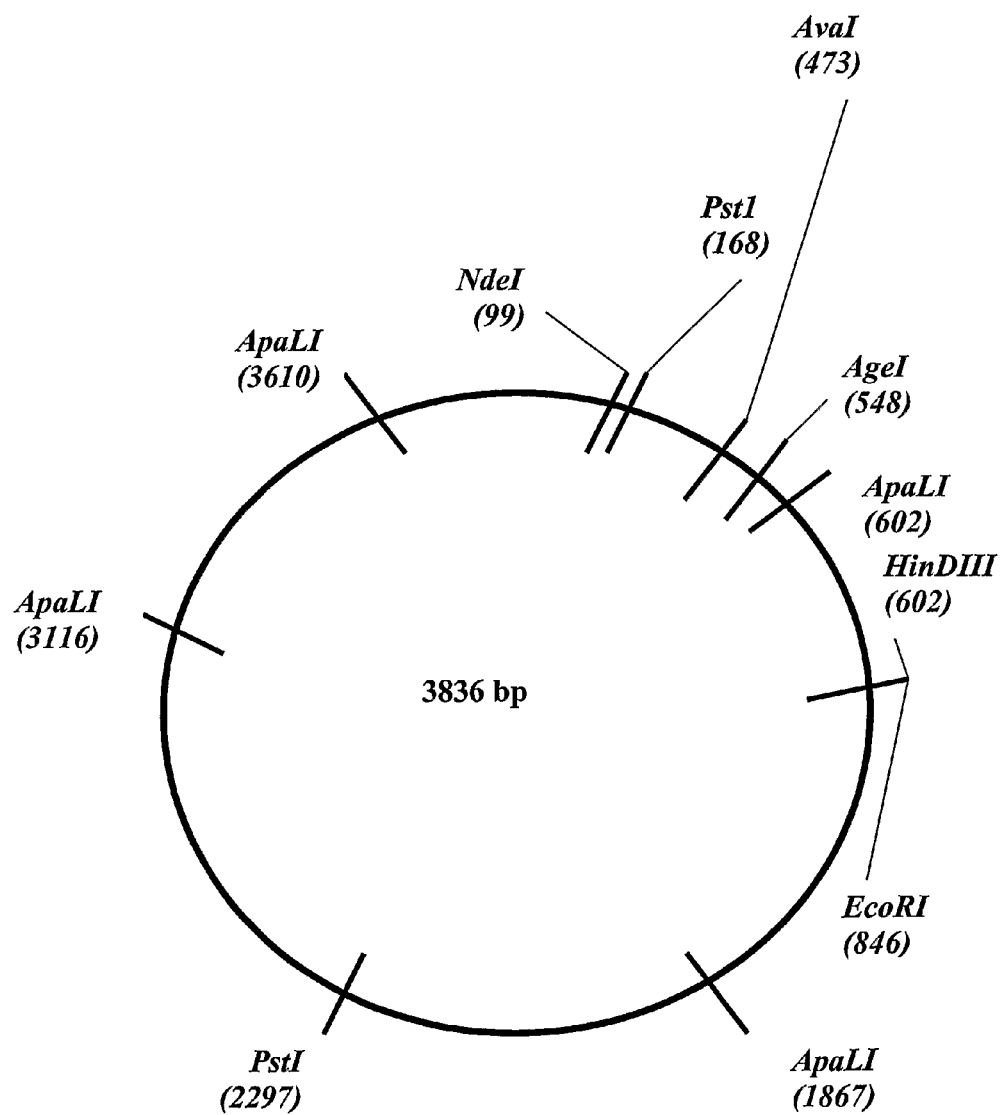
Figure 16:
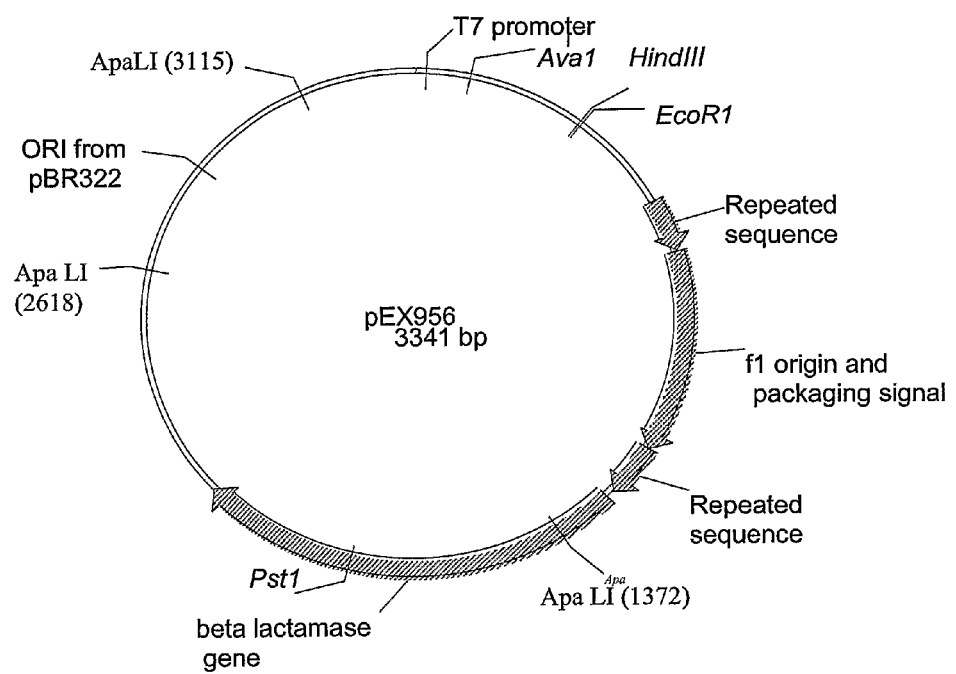

FIG. 10 is the DNA sequence of the pGMT7 plasmid.
FIG. 11 is the DNA sequence of the pEX954 plasmid.
FIG. 12 is the DNA sequence of the pEX821 plasmid.
FIG. 13 is the DNA sequence of the pEX956 plasmid.
FIG. 14 is the plasmid map of the pEX954 plasmid.
FIG. 15 is the plasmid map of the pEX821 plasmid.
FIG. 16 is the plasmid map of the pEX956 plasmid.

The inventors' approach was focussed on type 1 diabetes mellitus (T1DM) and was to create an artificial β cell in vitro, to isolate the HLA class 1 molecule and to release and identify the bound peptides. The inventors used a cell line (K526) that expresses no HLA class 1 molecules. The cell line was transfected with the genes encoding class I HLA-A2 and preproinsulin (PPI). The cells were then grown and the epitopes displayed on the HLA-A2 molecules were released. This method could be used for other cells involved in disease.

Overall Strategy

1. To artificially create by gene transfection a "β cell" that
   (a) makes and secretes PPI and (b) expresses only selected HLA class I molecules, in this case HLA-A2.
2. Grow this A2+PPI+ cell line in large amounts 3. Purify HLA-A2 from the surface and/or directly strip peptide repertoire from cell-surface HLA-A2
4. Identify HLA-A2-specific peptides using a subtractive approach (ie by comparison of peptide repertoire with A2+, PPI− cell line.
5. Take the peptides identified and examine using ELISPOT and Peptide-HLA tetramer approaches whether patients with T1DM have T cells that are active against these targets.
6. Clone CD8 T cells reactive against the peptide-HLA complex from patients with T1DM and obtain peptide-specific TCR sequences.

Example 1

Preparation of Artificial β Cells Transfected to Express HLA-A2 and PPI

Cloning Preproinsulin

PPI was cloned from cDNA freely obtained from Dr D F Steiner (Dept. Biochemistry and Molecular Biology, University of Chicago, Ill., USA) into the pcDNA6/myc-His B vector (Invitrogen, Paisley, UK), for expression in mammalian cell lines under blasticidin selection. The PPI gene was amplified by PCR using the primers PPI-forward (ATGGATC-CACCATGGCCCTGTGGATGCGC (SEQ ID NO: 11)) and PPI-reverse (GCGAATTCCTAGTTGCAGTAGTTCTC-CAGC (SEQ ID NO: 12)), and inserted following restriction enzyme digestion between the BamHI and EcoRI sites in the vector. Vectors were prepared by Qiagen maxiprep (Qiagen, Crawley, UK) for transfection. FIG. 1 provides amino acid sequence of human preproinsulin. The pre sequence is indicated by shading, the pro sequence (C peptide) is indicated by unaltered text, the B chain is indicated by underlining and the A chain is indicated by italic text.

K562 Cell Lines

K562 cells (a human erythroleukaemia tumour cell line that is negative for all surface HLA molecules) was obtained that expressed HLA-A2 (K562-A2) under Geneticin resistance following transfection with the HLA-A2 cDNA. These cells were obtained from Cedrik Britten, University of Mainz, Germany (Britten et al., (2002) *J. Immunol Methods* 259: 95-110) and cultured in RPMI 1640 medium supplemented with 10% heat-inactivated fetal bovine serum and 1% penicillin/streptomycin solution (all Invitrogen) at 37° C., 5% $CO_2$. Geneticin (Invitrogen) concentration in the medium was maintained at 0.7 mg ml$^{-1}$. The HLA-A2 molecule was expressed on ≥95% of cells as measured by flow cytometry, using an anti-HLA-A2 FITC antibody and FACSCalibur cytometer (Becton Dickinson, Oxford, UK).

Transfection

K562-A2 cells were transfected with PPI cDNA inserted into the pcDNA6/myc-His B vector prepared as described above using an Effectene kit (Qiagen) according to the manufacturer's instructions, adding 0.8 μg DNA (1.5 μl) to 6.4 μl Enhancer solution and 100 μl EC buffer, mixing by vortex for 1 min, and incubating at R/T for 5 minutes. 8 μl Effectene was then added, prior to a further 10 minute vortex, and incubation at R/T for 10 minutes. The mixture was then diluted with 600 μl RPMI, 10% FBS. During this time $2.1 \times 10^6$ K562-A2 cells were resuspended in 1.6 ml RPMI with 10% FBS. The transfection mixture was added to the cells, which were then incubated at 37° C. overnight. Cells were then washed 3 times (pelleting by centrifuge for 5 minutes R/T, 500×g) in RPMI, 10% FBS, and plated at 3 ml per well in 3 wells of a 24 well plate. After 24 hours incubation 2 ml medium was removed and 1 ml medium added (containing selection antibiotics for final working concentration of 0.7 mg ml$^{-1}$ Geneticin and 10 μg ml$^{-1}$ blasticidin). The transfected K562-A2 PPI cells were then maintained as for K562-A2 cells but with the addition of 10 μg ml$^{-1}$ blasticidin. After two weeks culture under selection, insulin, proinsulin and C-peptide were all detectable by ELISA (DRG International, Mountainside, N.J., USA) at 10-30 mU l$^{-1}$, >66 pM, and 200-300 pM respectively in the culture supernatants of K562-A2-PPI cells but not K562-A2 cells. Expression was stable for at least two months.

Example 2

Extraction of HLA-A2-Loaded Peptides from K562-A2 and K562-A2-PPI Cells

Peptides were extracted from the surface of cultured K562-A2 and K562-A2-PPI cells, prepared as described above, by citric acid elution as described in Storkus et al., (1993) *J Immunol* 151: 3719-27. Briefly, $4 \times 10^9$ cells were washed 3× in RPMI, pelleted into four tubes and finally resuspended in a total volume of 25 ml of pH 3.3 citrate-phosphate buffer (0.131 M citric acid, 0.066 M $Na_2HPO_4$) for 1 min at room temperature. Cells were then pelleted and the supernatant citric acid solution (containing previously cellular class I bound peptides) harvested and filtered through a 0.2 micron syringe filter. Two Sep-Pak C18 cartridges (Waters, Milford, Mass., USA) were connected in series and conditioned using 50 ml acetonitrile and then 50 ml citrate buffer. Supernatant was passed through the column. Peptides were eluted with 3 ml 80% acetonitrile per cartridge, and vacuum-dried to around 50 μl in volume. This residue was resuspended by adding a further 150 μl citrate buffer. Peptides were additionally purified by ultrafiltration through a 3 kDa MWCO Centricon-3 membrane (Millipore, Billerica Mass., USA) at 6500×g for 6 h at 18° C. The filtrate (approximately 100 μl) was stored at −80° C. prior to fractionation by RP-HPLC.

Acid extracted peptide filtrates were fractionated by reverse phase (RP) HPLC on a Symmetry C18 column (Waters) connected to a Waters 2690 Separations Module, 2487 Detector, and Fraction Collector. HPLC solvents were:
(A) water with 0.05% TFA and
(B) acetonitrile with 0.05% TFA.

Following a period of isocratic flow of (A) at a flow rate of 0.2 ml min$^{-1}$, 100 fractions were collected over a period from 20 mins to 120 mins, during which time the solvent gradient was increased from 100% (A) to 80% (B). Each 200 μl fraction was then vacuum-dried using a SpeedVac vacuum concentrator (Thermo) at R/T, to approximately 5-10 μl and stored at −80° C.

Example 3

Mass Spectrometry of Peptides Extracted from K562-A2 and K562-A2-PPI Cells

For Matrix Assisted Laser Desorption/Ionization Time of Flight (MALDI-TOF) analysis of peptides, 0.5 μl sample was mixed with 0.5 μl freshly prepared 2,5-dihydroxybenzoic acid matrix (MassPREP DHB matrix, Waters) or α-cyano-4-hydroxycinnamic acid matrix (CHCA, Bruker Daltonics, Billerica, Mass., USA) prepared at 10 mg ml$^{-1}$ in 1:1 (v/v) acetonitrile, 0.1% TFA. For internal calibration, a further 1 μl MS calibrant mixture was added, containing leu enkephalin (556.2771) 2.5 fmol and Substance P (1347.73543) 5 fmol. MS was performed using a Broker MALDI-TOF/TOF mass spectrometer. Samples were ionized using laser intensities in the range of ~5000 V and ~30,000 spectra acquired. Spectra were aligned with internal calibrants for maximum accuracy using linear calibration. This enabled an estimation of mass accuracy which was then used for matching putative unique masses to linear sequences of PPI. Putative unique sequences, i.e. those found in K562-A2-PPI but not control K562-A2 fractions, could then be identified either manually or using computer algorithms. Unique masses were then characterised by MS/MS to derive partial sequence information under collision-induced dissociation (CID) using atmospheric gas. The MS/MS spectrum for each fragmented unique mass is submitted to a local Mascot server to identify the precursor sequence from amongst the PPI sequence and human protein. (Perkins et al., (1999) *Electrophoresis* 20: 3551-67)

Results

Unique Masses Identified by MS

Figure 2:
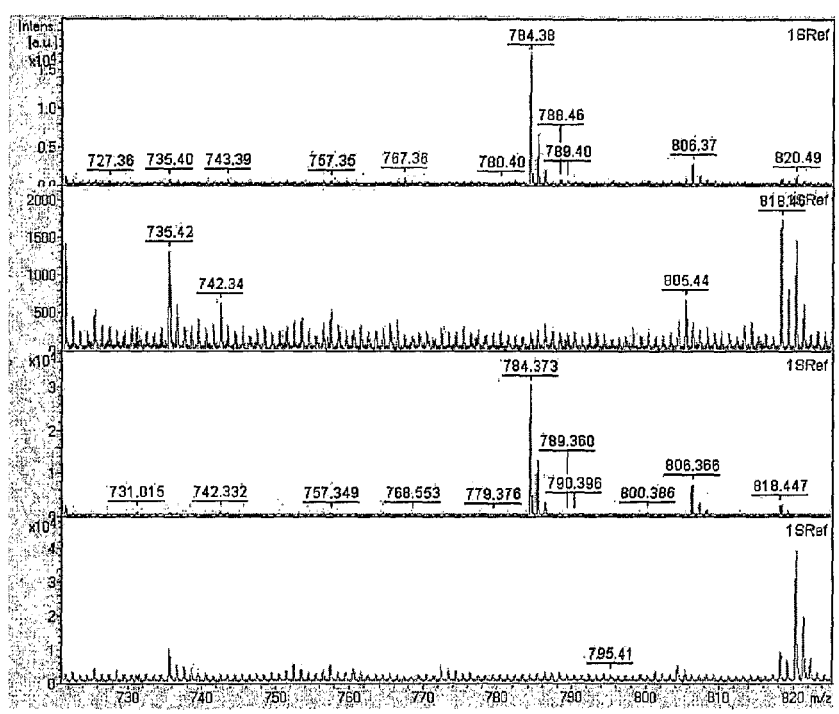
FIG. 2 is a mass spectrum showing the unique mass at m/z 784.37 A selection of the entire m/z spectrum analysed for two adjacent peptide fractions is shown. Traces from peptides derived from K562-A2-PPI are shown and reveal a unique mass at 784.37 not found in the control fractions from corresponding K562-A2 control fractions.

Two masses were identified as unique to the K562-A2-PPI cells and were not found in the control K562-A2 cell fractions. One of the unique masses reported was found mostly in fraction 55, and the other in fraction 65. The m/z of these unique masses was 784.37 and 968.48 respectively. The MS trace showing the unique mass 784.37 is shown in FIG. 2, and 968.48 in FIG. 3. These masses were matched to the PPI protein sequence, i.e. the potential peptide repertoire distinct to the K562-A2 PPI cells. Using the ExPASy FindPept software (http://au.expasy.org) these masses match most closely to the peptide sequences WGPDPAAA (SEQ ID NO: 4) ($PPI_{17-24}$) and ALWGPDPAAA (SEQ ID NO: 7) ($PPI_{15-24}$).

The fractions containing the unique masses were then analysed by MS/MS to confirm the identity of these masses by partial sequence information derived from CID fragmentation. The MS/MS window for fragmentation of m/z 784.37 is shown in FIG. 4, and m/z 968.48 in FIG. 5. The fragmentation patterns from MS/MS were uploaded to the Mascot server, which matches relative abundance of each ion to potential fragments for both the specific PPI sequence, and extensive human protein databases. The results of the Mascot analysis confirm the sequences initially identified by mass matching to the PPI sequence. In FIG. 6 the m/z 784.37 mass was confirmed by Mascot as the WGPDPAAA (SEQ ID NO: 4) sequence ($PPI_{17-24}$, SEQ ID NO:4), due to the distinct sequence of y and b ions produced by sequential fragmentation. In FIG. 7 the m/z 968.48 was confirmed as the overlapping ALWGPDPAAA (SEQ ID NO: 7) peptide, again with a clear series of y and b ion fragmentation.

Example 4

Cytokine ELISPOTS

The following ELISPOT assays were carried out using the methods substantially as described in Arif et al., (2004) *J Clin Invest* 113: 451-63.

Fresh peripheral blood mononuclear cells (PBMCs) in RPMI 1640 supplemented with antibiotics (TC medium; all Life Technologies) and 10% human AB serum (Harlan SeraLab, Leicestershire, UK) were dispensed into 48-well plates at a density of $2\times10^6$ cells in 0.5 ml supplemented with peptide to a final concentration of 10 µM and incubated at 37° C., 5% $CO_2$, tilted by 5°. Control wells comprised TC medium containing an equivalent concentration of peptide diluent alone (DMSO). On day +1, 0.5 ml pre-warmed TC medium/10% AB was added and on day +2, non-adherent cells were re-suspended using pre-warmed TC medium/2% AB, washed, brought to a concentration of $1\times10^6$ cells/300 µl and 100 µl dispensed in triplicate into wells of 96-well ELISA plates (Nunc Maxisorp, Merck, Poole, UK) pre-blocked with 1% BSA in PBS and pre-coated with monoclonal anti-IFN-γ capture antibody (U-Cytech, Utrecht, NL). After capture at 37° C., 5% $CO_2$ for 7 hours, cells were lysed in ice cold water, plates washed in PBS/Tween 20 and spots developed according to the manufacturer's instructions. Plates were dried and spots of 80-120 µm counted in a BioReader 3000 (BioSys, Karben, Germany).

Triplicate values were pooled to provide mean (SEM) spots per 300,000 cells, the approximate number of PBMCs from the bulk starter culture for each ELISPOT well. Mean values in test wells were compared with means of the background (DMSO) wells to derive a stimulation index (SI).

Results

In patients with new-onset type 1 diabetes and HLA-A2 we were able to demonstrate the presence of CD8 T cells specific for the $PPI_{15-24}$ and $PPI_{17-24}$ peptides (FIG. 8*a*). Overall, responses are more frequent in patients with type 1 diabetes and HLA-A2 compared with HLA-A2 non-diabetic control subjects (FIG. 8*b*). Moreover, the CD8 cells reactive against $PPI_{15-24}$ and $PPI_{17-24}$ peptides can be isolated, cloned, and exhibit specific killing of human HLA-A2+ beta cells, indicating that the epitopes are presented naturally on human beta cells.

In summary, the inventors have used a novel technology to address the questions of what peptide fragments of the diabetes-related autoantigen preproinsulin are presented through the HLA class I pathway, and whether these have disease relevance. The inventors identify unequivocally by micro-sequencing two such peptide fragments located in the signal sequence, which are unique to the preproinsulin molecule. Synthetic forms of these peptides are recognised by effector memory CD8 T cells in patients with type 1 diabetes and could therefore represent important targets of the immune response in this disease.

Example 5

Production and Testing of HLA-A*0201 Complexes Loaded with Peptides Derived from Human PPI Production of HLA-A*0201 Complexes Loaded with Human Preproinsulin Peptides Biotinylated HLA-A*0201 complexes loaded with human preproinsulin peptides are refolded in vitro from bacterially-expressed inclusion bodies containing the constituent subunit proteins and synthetic peptide, followed by purification and in vitro enzymatic biotinylation (O'Callaghan et al. (1999) *Anal. Biochem.* 266: 9-15). HLA-A*0201 heavy chain is expressed with a C-terminal biotinylation tag which replaces the transmembrane and cytoplasmic domains of the protein in an appropriate construct. Inclusion body expression levels of ~75 mg/liter bacterial culture are obtained. The HLA light-chain or β2-microglobulin is also expressed as inclusion bodies in *E. coli* from an appropriate construct, at a level of ~500 mg/liter bacterial culture.

*E. coli* cells are lysed and inclusion bodies are purified to approximately 80% purity. Protein from inclusion bodies is denatured in 6 M guanidine-HCl, 50 mM Tris pH 8.1, 100 mM NaCl, 10 mM DTT, 10 mM EDTA, and then refolded at a concentration of 30 mg/liter heavy chain, 30 mg/liter η2 m into 0.4 M L-Arginine-HCl, 100 mM Tris pH 8.1, 3.7 mM cystamine, 6.6 mM β-cysteamine, 4 mg/ml preproinsulin peptide (for example, WGPDPAAA (SEQ ID NO: 4) or ALWGPDPAAA (SEQ ID NO: 7)), by addition of a single pulse of denatured protein into refold buffer at <5° C. Refolding is allowed to reach completion at 4° C. for at least 1 hour.

Buffer is exchanged by dialysis in 10 volumes of 10 mM Tris pH 8.1. Two changes of buffer are necessary to reduce the ionic strength of the solution sufficiently. The protein solution is then filtered through a 1.5 μm cellulose acetate filter and loaded onto a POROS 50HQ anion exchange column (8 ml bed volume). Protein is eluted with a linear 0-500 mM NaCl gradient. HLA-A2-peptide complex eluted at approximately 250 mM NaCl, and peak fractions are collected, a cocktail of protease inhibitors (Calbiochem) is added and the fractions are chilled on ice.

Biotinylation tagged HLA complexes are buffer exchanged into 10 mM Tris pH 8.1, 5 mM NaCl using a Pharmacia fast desalting column equilibrated in the same buffer. Immediately upon elution, the protein-containing fractions are chilled on ice and protease inhibitor cocktail (Calbiochem) is added. Biotinylation reagents are then added: 1 mM biotin, 5 mM ATP (buffered to pH 8), 7.5 mM $MgCl_2$, and 5 μg/ml BirA enzyme (purified according to O'Callaghan et al. (1999) *Anal. Biochem.* 266: 9-15). The mixture is then allowed to incubate at room temperature overnight.

Biotinylated HLA complexes are purified using gel filtration chromatography. A Pharmacia Superdex 75 HR 10/30 column is pre-equilibrated with filtered PBS and 1 ml of the biotinylation reaction mixture is loaded and the column is developed with PBS at 0.5 ml/min. Biotinylated HLA complexes elute as a single peak at approximately 15 ml. Fractions containing protein are pooled, chilled on ice, and protease inhibitor cocktail is added. Protein concentration is determined using a Coomassie-binding assay (PerBio) and aliquots of biotinylated HLA complexes are stored frozen at −20° C.

Tetramers of the biotinylated peptide-HLA-A*0201 complexes can then be produced by the addition of Streptavidin at a ratio of 4:1 peptide-HLA-A*0201: Streptavidin. A detailed description of the production of suitable HLA tetramers can be found in WO 96/26962.

Example 6

Preparation of Pre Proinsulin (PPI) Peptide-HLA-A2 Specific Polyclonal T Cell Lines Reagents:

| | |
|---|---|
| RPMI 1640 media | (Invitrogen 42401-091) |
| Iscoves media | (Invitrogen 12440-053) |
| Glutamine | (Invitrogen 25030-024) |
| Penicillin/Streptomycin (Pen/Strep) | (Invitrogen 15070-063) |
| AB serum | (TCS Biologicals Z2CS300) |
| Proleukin (modified IL-2) | (Chiron) |
| IL-7 | (Peprotec 200-07) |
| Transferrin | (Boehringer 652 202) |
| Insulin | (Sigma 12767) |
| GM-CSF | (Peprotec 300-03) |
| IL-4 | (Peprotec 200-04) |
| Poly I:C | (Sigma P0913) |
| Cyclosporin A | (Sigma C3662) |
| PHA-M | (Sigma L8902) |

Method:

$CD8^+$ T cells are enriched from a peripheral blood mononucleate cell (PBMC) population by magnetic separation. 1-2×10⁶ "$CD8^+$ T Cells" in RPMI media+10% AB serum+1% Glutamine+1% Pen/Strep (R+10AB) are placed into the each well of a 24 well plate. (Nunc)

First Cell Stimulation

The first cell stimulation of the CD8+ T cells is carried out using dendritic cells (DCs) which are isolated from PBMC by adherence to 10 cm tissue culture dishes. DCs are matured in RPMI media containing 5% AB serum, 1% Glutamine, 1% Pen/Strep, 50 μg/ml transferrin, 5 μg/ml insulin, 50 ng/ml GM-CSF, 100 ng/ml IL-4, 12.5 μg/ml poly I:C for ~7 days. The DCs are harvested and washed in R+10AB media and then re-suspended in 5 ml of R+10AB media 10 μg/ml PPI peptide is then added to the DCs which are incubated for 2 hours at 37° C. The excess PPI peptide is washed off and the DCs are re-suspended in a sufficient volume of R+10AB media to supply the cells in a 1 ml volume to each well delivering the required ratio of $CD8^+$ T cells: DCs. This ratio is varied from 1:1 to 20:1 $CD8^+$ T cells:DCs IL-7 is added to each well to give a final concentration of 10 ng/ml and the cells are incubated at 37° C., 5% $CO_2$. 50 Units/ml Proleukin is then added to each well after 48 hours incubation. The cells are then cultured at 37° C., with fresh R+10AB media+Proleukin every 2-3 days.

Subsequent Cell Stimulations 1 week after the initial cell stimulation the cells are then re-stimulated using either peptide-pulsed DCs as described above, or autologous CD40L activated B cells as described below. Cell stimulation is then repeated a total of 4-5 times at 1-2 weekly intervals depending on culture expansion.

The CD40L activated B cells required for stimulation of the CD8+ T cells are generated by harvesting autologous PBMCs which have been cultured with an irradiated (96Gy) monolayer of NIH 3T3hCD40L cells (Dana Farber Inst.) in Iscoves media containing 10% AB serum, 1% Glutamine, 1% Pen/Strep, 50 μg/ml transferrin, 5 μg/ml insulin, 20 ng/ml IL-4, 0.55 μM cyclosporin A. (The NIH 3T3hCD40L cells are NIH 3T3 cells which have been transfected to express CD40L). The activated B cells are transferred to a fresh monolayer of irradiated NIH 3T3hCD40L cells twice a week with fresh media. The cells can be used for stimulation when the culture contains >95% B cells.

A viable cell count is carried out on the CD40L activated B cells and dead cells are removed by running the B cells on a Lyphoprep gradient. Any remaining 3T3CD40L cells are removed by a further 20 min adherent step. The remaining B cells are then recounted.

The CD8+ T cells are then re-stimulated using the CD40L activated B cells (4:1 T:B ratio) as follows:

2×10⁶ CD8+ T cells in 1 ml R+10AB media are placed in the wells of a 24 well plate.

5×10⁵ B Cells are re-suspend in 1 ml R+10AB with 10 μg/ml PPI peptide and incubated for 2 hours at 37° C. in R+10AB, during which time the cells are irradiated at 33Gy. Excess peptide is then washed off and the B cells are re-suspended in R+10AB so that 1 ml contains 5×10⁵ B cells supplying a ratio of 4:1 $CD8^+$ T cells:B cells The cells are then incubated at 37° C., 5% $CO_2$, 50 Units/ml Proleukin is then added to each well after 48 hours incubation. The cells are then cultured at 37° C., 5% $CO_2$ with fresh R+10AB media+ Proleukin every 2-3 days.

Example 7

Preparation of Pre Proinsulin (PPI) Peptide-HLA-A*0201 Specific T-Cell Clones from the Polyclonal T Cell Lines Prepared in Example 6

The following example is based substantially the methods detailed in Dunbar et al., (1999) *J. Immunol*, 162 p 6959-6962.

Production of Peripheral Blood Mononuclear Cells (PBMC)-Feeders

Round bottom 96 well plates are coated with anti-CD3 (BD Pharmingen Cat No. 555329) and anti-CD28 (BD Pharmingen Cat No. 555725) antibodies, both at 100 ng/ml in PBS.

PBMCs are washed twice with R+10AB media in 20 ml tubes ($2.5 \times 10^7$ PBMC/tube) and centrifuged at 1200 rpm (Megafuge 1.0R, Heraeus) for 10 minutes. The PBMCs are then re-suspended and irradiated. (30Gy) A mixture of 3 different PBMCs derived from a range of buffy coats samples are used. $10^7$ PBMC are added to each 96 well plate ($10^5$ irradiated PBMC/well in 100 μl R+10AB media containing 20 Units/ml Proleukin and 5 μg/ml PHA-M).

The 96 well plates are allowed to equilibrate at 37° C., 5% $CO_2$ for at least 1 h before cell sorting is carried out.

Cloning from T-Cell Lines using PPI Peptide-HLA-A*0201 Tetramers

The re-stimulated PPI peptide-HLA-A*0201-specific polyclonal T-cell lines, prepared as described in Example 6, are not fed for at least two days prior to staining with tetramer. T-cell clones are isolated using PPI peptide-HLA-A*0201 tetramers, produced as described in Example, 5. For staining with PPI peptide-HLA-A*0201 tetramers, polyclonal T cell lines are spun down in a FACS tube and re-suspended in their residual volume (approximately 50 μl). The polyclonal T cell lines are then incubated in the presence of PPI peptide-HLA-A*0201 PE labelled tetramer (giving a final concentration of 10 μg/ml) at 37° C., 5% $CO_2$ for 30 minutes before being washed in RPMI. 3 μl of anti CD8 FITC labelled antibody (BD Biosciences) is then added to each well and left for a further 10 minutes. The cells are then washed once in RPMI and centrifuged at 1500 rpm (Megafuge 1.0R, Heraeus) for 10 minutes. The supernatant is then discarded and the cells re-suspended in approximately 500 μl of RPMI. Double positive ($CD8^+$ and PPI peptide-HLA-A*0201 $tetramer^+$ stained) cells are sorted in to 96 well plates on to feeder cells prepared as described above. (1-3 T cells per well)

Screening of T-Cell Clones

After 14 days the 96 well plates are screened for T cell clones. Each well of each 96 well plates is examined for signs of T cell proliferation by phase microscopy. Any T cell clones identified are then re-stimulated by PHA and Proleukin or IL-15 (Peprotech).

Example 8

A Method for the Production of DNA Encoding a Soluble Disulfide-Linked TCR which Binds to Class I HLA-A*0201 Complexes Loaded with a Peptide Derived from Human Pre-Proinsulin RNA Isolation Total RNA is isolated from $1 \times 10^5$ clonal T cells derived from the T cells isolated using the method described in Example 7. The Qiagen RNeasy Micro kit is used to prepare total RNA according to the manufacturer's protocols.

Rescue of TCR V Alpha and V Beta Chains from T-Cell RNA

The TCR V alpha and V beta chains are rescued from the T-cell line RNA using the Invitrogen 5' RACE system for rapid amplification of cDNA ends. The rescue of the TCR chains is carried out as described in the kit manufactures protocol.

The kit describes the use of gene specific primers (GSP) for the TCR alpha chain these gene specific primers are

```
                                      (SEQ ID NO: 13)
      GSP1-catcagaatccttactttgtg (SEQ ID NO: 14)
      GSP2-taggcagacagacttgtcact (SEQ ID NO: 15)
      GSP3 gatttagagtctctcagctggt
```

For the TCR beta chain these gene specific primers are

```
                                      (SEQ ID NO: 16)
      GSP1          tggtcggggaagaagcctgtg (SEQ ID NO: 17)
      GSP2          gccttttgggtgtgggagatc (SEQ ID NO: 18)
      GSP3          tgatggctcaaacacagcgacc
```

Subsequent to the GSP2 PCRs it is necessary to carry out an additional PCR for both the TCR alpha and beta chains with GSP3 to generate enough PCR product to clone. The PCR products are cloned into Promegas pGEM T-Vector system. T vector clones containing either the v alpha of v beta chains are grown up and plasmid DNA prepared using standard DNA plasmid miniprep procedures. The DNA is then sent for sequencing.

The wild-type DNA encoding the TCR alpha and beta chains isolated and sequenced as described above is then used as a PCR template to prepare DNA encoding soluble analogues of the two chains which each include an introduced non-native cysteine encoding codon to facilitate association of the of the TCR chains in-vitro. The sequences of the TCR alpha and beta chain encoding DNA isolated and identified as above are used to determine which TCR variable region-specific forward primers are used for the PCR amplifications. The NCBI website provides a list of primers suitable for the amplification of TCR chain encoding genes comprising all known TCR variable domain genes. The selected primers are further modified as follows:

The sequences of the chosen primers are 5-prime optimised for expression in *E. coli* by reducing their GC usage.

The TCR alpha chain forward primers are designed to contain a restriction site suitable for cloning the DNA sequence into an expression vector. The choice of which restriction site to include is made by inspection of the DNA sequence encoding the wild-type TCR alpha chain to ensure that the portion of the DNA that is to be amplified does not contain the recognition site to be utilised. The other primer required to amplify the required portion of the TCR alpha chain-encoding DNA is a universal alpha-chain reverse primer incorporating a SalI restriction site.

The TCR beta chain forward primers are designed to contain a restriction site suitable for cloning the DNA sequence into an expression vector. The choice of which restriction site to include is made by inspection of the DNA sequence encoding the wild-type TCR beta chain to ensure that the portion of the DNA that is to be amplified does not contain the recognition site to be utilised. The other primer required to amplify the required portion of the TCR alpha chain-encoding DNA is a universal alpha-chain reverse primer incorporating a AgeI restriction site.

Recipient vectors for the TCR gene fragments are based on a pGMT7 parent plasmid (FIG. 10 provides the DNA sequence of the pGMT7 plasmid), which contains the T7 promoter for high level expression in *E. coli* cells.

The alpha chain purified PCR products are then digested with the appropriate restriction enzyme, chosen as described, above, and SalI and ligated into pEX954 (FIGS. 11 and 14 show the DNA sequence and plasmid map of pEX954 respectively) or pEX956 (FIGS. 13 and 16 show the DNA sequence and plasmid map of pEX956 respectively)

TCR beta chain purified PCR products are then digested with the appropriate restriction enzyme, chosen as described above, and AgeI and ligated into pEX821 (FIGS. 12 and 13 show the DNA sequence and plasmid map of pEX821 respectively)

Ligation

Each cut PCR product and the corresponding cut vector are ligated using a rapid DNA ligation kit (Roche) following the manufacturer's instructions.

Ligated plasmids are transformed into competent *E. coli* cells and plated out on LB/agar plates containing 100 μg/ml ampicillin. Following incubation overnight at 37° C., single colonies are picked and grown in 10 ml LB containing 100 μg/ml ampicillin overnight at 37° C. with shaking. Cloned plasmids are purified using a Miniprep kit (Qiagen) and the insert is sequenced using an automated DNA sequencer (Lark Technologies).

Example 9

Expression, Refolding and Purification of Soluble Disulfide-Linked PPI Peptide-HLA-A2 Specific TCRs The expression plasmids containing the DNA encoding TCR α-chain and β-chain respectively as prepared in Example 8 are transformed separately into *E. coli* cells and single antibiotic-resistant colonies are grown at 37° C. in TYP (ampicillin 100 μg/ml, chloramphenicol (15 μg/ml) and 1% w/v glucose) medium to $OD_{600}$ of 0.4 before inducing protein expression with 0.5 mM IPTG. Cells are harvested three hours post-induction by centrifugation for 30 minutes at 4000 rpm in a Beckman J-6B. Cell pellets are re-suspended in approximately 15 ml of Bugbuster solution (Novagen), supplemented with 20 μg/ml DNAse, 10 mM $MgCl_2$, for each liter of culture used to produce the cell pellet and the culture are mixed on a magnetic stirrer for 30-60 minutes. The cultures are then subjected to a freeze-thaw cycle to assist complete cell lysis. The cultures are then spun at 4000 rpm (Megafuge 2.0R, Heraeus).

Inclusion body pellets are recovered by centrifugation for 30 minutes at 4000 rpm (Megafuge 2.0R, Heraeus). Three detergent washes are then carried out to remove cell debris and membrane components. Each time the inclusion body pellet is homogenised in a Triton buffer (50 mM Tris-HCl, 0.5% Triton-X100, 200 mM NaCl, 10 mM NaEDTA, 2 mM DTT, pH 8.1) before being pelleted by centrifugation for 30 minutes at 4000 rpm (Megafuge 2.0R, Heraeus). Detergent and salt is then removed by a similar wash in the following buffer: 50 mM Tris-HCl, 100 mM NaCl, 10 mM NaEDTA, 2 mM DTT, pH 8.1. Finally, the inclusion bodies are divided into 30 mg aliquots and frozen. Inclusion body protein yield is quantitated by solubilising with 6M guanidine-HCl and measurement by spectrophotometry at 280 nm.

Approximately 30 mg of TCR β chain and 60 mg of TCR α chain solubilised inclusion bodies are thawed from frozen stocks, samples are then mixed and the mixture diluted into 15 ml of a guanidine solution (6M Guanidine-hydrochloride, 50 mM Tris-HCl, 100 mM NaCl, 10 mM NaEDTA, 10 mM DTT, pH 8.1.), to ensure complete chain denaturation. This solution is then left to incubate at 37° C. for 30 minutes. The guanidine solution containing fully reduced and denatured TCR chains is then injected into 1 liter of the following refolding buffer: 100 mM Tris pH 8.1, 400 mM L-Arginine, 10 mM EDTA, 5M urea. The redox couple, 2-mercaptoethylamine and cystamine (to final concentrations of 6.6 mM and 3.7 mM, respectively) are added approximately 5 minutes before addition of the denatured TCR chains. The solution was left for at least one hour. The refolded TCR is dialysed in Spectrapor 1 membrane (Spectrum; Product No. 132670) against 10 L 10 mM Tris pH 8.1 at 5° C.±3° C. for 18-20 hours. After this time, the dialysis buffer is changed to fresh 10 mM Tris pH 8.1 (10 L) and dialysis is continued at 5° C.±3° C. for another 20-22 hours. The dialysis buffer is changed at least one further time and dialysis is continued at 5° C.±3° C. for another 20-22 hours.

sTCR is separated from degradation products and impurities by loading the dialysed refold onto an anion exchange column and eluting bound protein with a gradient of 0-500 mM NaCl over 5 column volumes using an AKTA purifier (GE Healthcare) or FPLC. Peak fractions are stored at 4° C. and analysed by Coomassie-stained SDS-PAGE before being pooled and concentrated. Finally, the sTCR is purified and characterised using a Superdex 75HR gel filtration column pre-equilibrated in HBS-EP buffer (10 mM HEPES pH 7.4, 150 mM NaCl, 3.5 mM EDTA, 0.05% nonidet p40). The peak eluting at a relative molecular weight of approximately 50 kDa is pooled and concentrated prior to characterisation by BIAcore surface plasmon resonance analysis.

Example 10

Biacore Surface Plasmon Resonance Characterisation of sTCR Binding to Specific pMHC A surface plasmon resonance biosensor (Biacore 3000™) is used to analyse the binding of the sTCR prepared as above to its ALWGPDPAAA (SEQ ID NO: 7)-HLA-A2 ligand. This is facilitated by producing biotinylated pMHC monomers (using the methods described in Example 5) which are immobilised to a streptavidin-coated binding surface in a semi-oriented fashion, allowing efficient testing of the binding of a soluble T-cell receptor to up to four different pMHC (immobilised on separate flow cells) simultaneously. Manual injection of HLA complex allows the precise level of immobilised class I molecules to be manipulated easily.

The pMHC binding properties of the sTCR are observed to be qualitatively and quantitatively similar if the sTCR is used either in the soluble or immobilised phase. This is an important control for partial activity of soluble species and also suggests that biotinylated pMHC complexes are biologically as active as non-biotinylated complexes.

The interactions between the sTCR containing a novel inter-chain bond and its ligand/MHC complex or an irrelevant HLA-peptide combination are analysed on a Biacore 3000™ surface plasmon resonance (SPR) biosensor. SPR measures changes in refractive index expressed in response units (RU) near a sensor surface within a small flow cell, a principle that can be used to detect receptor ligand interactions and to analyse their affinity and kinetic parameters. The probe flow cells are prepared by immobilising the individual HLA-peptide complexes in separate flow cells via binding between the biotin cross linked onto β2m and streptavidin which have been chemically cross linked to the activated surface of the flow cells. The assay is then performed by passing the sTCR over the surfaces of the different flow cells at a constant flow rate, measuring the SPR response in doing so.

To Measure Equilibrium Binding Constant

Serial dilutions of the sTCR are prepared and injected at constant flow rate of 5 µl min-1 over two different flow cells; one coated with ~1000 RU of the cognate HLA-A*0201 complex, the second coated with ~1000 RU of a non-specific HLA-A2-peptide complex. Response is normalised for each concentration using the measurement from the control cell. Normalised data response is plotted versus concentration of TCR sample and fitted to a hyperbola in order to calculate the equilibrium binding constant, $K_D$. (Price & Dwek, Principles and Problems in Physical Chemistry for Biochemists ($2^{nd}$ Edition) 1979, Clarendon Press, Oxford).

To Measure Kinetic Parameters

For the sTCR $K_D$ can be determined by experimentally measuring the dissociation rate constant, kd, and the association rate constant, ka. The equilibrium constant $K_D$ is calculated as kd/ka.

The sTCR is injected over two different cells one coated with ~300 RU of the HLA-A2-ALWGPDPAAA complex, the second coated with ~300 RU of non-specific HLA-A2-peptide complex. Flow rate is set at 50 µl/min. Typically 250 µl of TCR at ~3 µM concentration is injected. Buffer is then flowed over until the response returns to baseline. Kinetic parameters are calculated using Biaevaluation software. The dissociation phase is also fitted to a single exponential decay equation enabling calculation of half-life.

The invention claimed is:

1. An isolated soluble dimeric T cell receptor (dTCR) having specific binding affinity for a peptide-MHC complex wherein the MHC is an HLA-A*0201 Class I molecule and the peptide is a preproinsulin-derived peptide of 8 to 10 amino acids, comprising the amino acid sequence WGPDPAA (SEQ ID NO: 1).

2. The isolated molecule of claim 1, which is a soluble dimeric T cell receptor (dTCR) having specific binding affinity for a peptide-MHC complex wherein the MHC is an HLA-A*0201 Class 1 molecule and the peptide is a preproinsulin-derived peptide consisting of the amino acid sequence WGPDPAAA (SEQ ID NO: 4)- or ALWGPDPAAA (SEQ ID NO: 7).

3. The isolated dTCR of claim 1, comprising both a TCR α chain variable domain and a TCR β chain variable domain.

4. The isolated dTCR of claim 1, comprising a first polypeptide wherein a sequence corresponding to a TCR α chain variable region sequence is fused to the N terminus of a sequence corresponding to a TCR α chain constant domain extracellular sequence, and
a second polypeptide wherein a sequence corresponding to a TCR β chain variable region sequence fused to the N terminus a sequence corresponding to a TCR β chain constant domain extracellular sequence,
the first and second polypeptides being linked by a disulfide bond between cysteine residues substituted for Thr 48 of exon 1 of TRAC*01 and Ser 57 of exon 1 of TRBC1*01 or TRBC2*01 or the non-human equivalent thereof.

5. The isolated soluble dTCR of claim 1, which further comprises an immunomodulatory agent or imaging agent.

6. The isolated soluble dTCR of claim 5, wherein the immunomodulatory agent is an immunosuppressive agent selected from one of IL-4, IL-10 or IL-13.

7. The isolated dTCR of claim 2, comprising both a TCR α chain variable domain and a TCR β chain variable domain.

8. The isolated dTCR of claim 2, comprising a first polypeptide wherein a sequence corresponding to a TCR α chain variable region sequence is fused to the N terminus of a sequence corresponding to a TCR α chain constant domain extracellular sequence, and a second polypeptide wherein a sequence corresponding to a TCR β chain variable region sequence fused to the N terminus a sequence corresponding to a TCR β chain constant domain extracellular sequence, the first and second polypeptides being linked by a disulfide bond between cysteine residues substituted for Thr 48 of exon 1 of TRAC*01 and Ser 57 of exon 1 of TRBC1*01 or TRBC2*01 or the non-human equivalent thereof.

9. The isolated soluble TCR of claim 2, which further comprises an immunomodulatory agent or imaging agent.

10. The isolated soluble dTCR of claim 9, wherein the immunomodulatory agent is an immunosuppressive agent selected from one of IL-4, IL-10 or IL-13.

11. The isolated dTCR of claim 3, comprising a first polypeptide wherein a sequence corresponding to a TCR α chain variable region sequence is fused to the N terminus of a sequence corresponding to a TCR α chain constant domain extracellular sequence, and a second polypeptide wherein a sequence corresponding to a TCR β chain variable region sequence fused to the N terminus a sequence corresponding to a TCR β chain constant domain extracellular sequence, the first and second polypeptides being linked by a disulfide bond between cysteine residues substituted for Thr 48 of exon 1 of TRAC*01 and Ser 57 of exon 1 of TRBC1*01 or TRBC2*01 or the non-human equivalent thereof.

12. The isolated soluble dTCR of claim 3, which further comprises an immunomodulatory agent or imaging agent.

13. The isolated soluble dTCR of claim 12, wherein the immunomodulatory agent is an immunosuppressive agent selected from one of IL-4, IL-10 or IL-13.

* * * * *

SEQUENCE LISTING

```
<160> NUMBER OF SEQ ID NOS: 23

<210> SEQ ID NO 1
<211> LENGTH: 7
<212> TYPE: PRT
<213> ORGANISM: Homo sapien
<220> FEATURE:
<223> OTHER INFORMATION: amino acids 17-23 of preproinsulin

<400> SEQUENCE: 1

Trp Gly Pro Asp Pro Ala Ala
1               5

<210> SEQ ID NO 2
<211> LENGTH: 9
<212> TYPE: PRT
<213> ORGANISM: Artificial
<220> FEATURE:
<223> OTHER INFORMATION: Synthesized

<400> SEQUENCE: 2

Ala Leu Trp Gly Pro Asp Pro Ala Ala
1               5

<210> SEQ ID NO 3
<211> LENGTH: 8
<212> TYPE: PRT
<213> ORGANISM: Artificial
<220> FEATURE:
<223> OTHER INFORMATION: Synthesized

<400> SEQUENCE: 3

Leu Trp Gly Pro Asp Pro Ala Ala
1               5

<210> SEQ ID NO 4
<211> LENGTH: 8
<212> TYPE: PRT
<213> ORGANISM: Artificial
<220> FEATURE:
<223> OTHER INFORMATION: Synthesized

<400> SEQUENCE: 4

Trp Gly Pro Asp Pro Ala Ala Ala
1               5

<210> SEQ ID NO 5
<211> LENGTH: 9
<212> TYPE: PRT
<213> ORGANISM: Artificial
<220> FEATURE:
<223> OTHER INFORMATION: Synthesized
```

<400> SEQUENCE: 5

Trp Gly Pro Asp Pro Ala Ala Ala Phe
1               5

<210> SEQ ID NO 6
<211> LENGTH: 9
<212> TYPE: PRT
<213> ORGANISM: Artificial
<220> FEATURE:
<223> OTHER INFORMATION: Synthesized

<400> SEQUENCE: 6

Leu Trp Gly Pro Asp Pro Ala Ala Ala
1               5

<210> SEQ ID NO 7
<211> LENGTH: 10
<212> TYPE: PRT
<213> ORGANISM: Artificial
<220> FEATURE:
<223> OTHER INFORMATION: Synthesized

<400> SEQUENCE: 7

Ala Leu Trp Gly Pro Asp Pro Ala Ala Ala
1               5                   10

<210> SEQ ID NO 8
<211> LENGTH: 10
<212> TYPE: PRT
<213> ORGANISM: Artificial
<220> FEATURE:
<223> OTHER INFORMATION: Synthesized

<400> SEQUENCE: 8

Leu Ala Leu Trp Gly Pro Asp Pro Ala Ala
1               5                   10

<210> SEQ ID NO 9
<211> LENGTH: 10
<212> TYPE: PRT
<213> ORGANISM: Artificial
<220> FEATURE:
<223> OTHER INFORMATION: Synthesized

<400> SEQUENCE: 9

Leu Trp Gly Pro Asp Pro Ala Ala Ala Phe
1               5                   10

<210> SEQ ID NO 10
<211> LENGTH: 10
<212> TYPE: PRT
<213> ORGANISM: Artificial
<220> FEATURE:
<223> OTHER INFORMATION: Synthesized

<400> SEQUENCE: 10

Trp Gly Pro Asp Pro Ala Ala Ala Phe Val
1               5                   10

<210> SEQ ID NO 11
<211> LENGTH: 29
<212> TYPE: DNA
<213> ORGANISM: Artificial
<220> FEATURE:
<223> OTHER INFORMATION: Primer, Synthesized

<400> SEQUENCE: 11
atggatccac catggccctg tggatgcgc                                29

<210> SEQ ID NO 12
<211> LENGTH: 30
<212> TYPE: DNA
<213> ORGANISM: Artificial
<220> FEATURE:
<223> OTHER INFORMATION: Primer, Synthesized

<400> SEQUENCE: 12
gcgaattcct agttgcagta gttctccagc                               30

<210> SEQ ID NO 13
<211> LENGTH: 21
<212> TYPE: DNA
<213> ORGANISM: Artificial
<220> FEATURE:
<223> OTHER INFORMATION: Primer, Synthesized

<400> SEQUENCE: 13
catcagaatc cttactttgt g                                        21

<210> SEQ ID NO 14
<211> LENGTH: 21
<212> TYPE: DNA
<213> ORGANISM: Artificial
<220> FEATURE:
<223> OTHER INFORMATION: Primer, Synthesized

<400> SEQUENCE: 14
taggcagaca gacttgtcac t                                        21

<210> SEQ ID NO 15
<211> LENGTH: 22
<212> TYPE: DNA
<213> ORGANISM: Artificial
<220> FEATURE:
<223> OTHER INFORMATION: Primer, Synthesized

<400> SEQUENCE: 15
gatttagagt ctctcagctg gt                                       22

<210> SEQ ID NO 16
<211> LENGTH: 21
<212> TYPE: DNA
<213> ORGANISM: Artificial
<220> FEATURE:
<223> OTHER INFORMATION: Primer, Synthesized

<400> SEQUENCE: 16
tggtcgggga agaagcctgt g                                        21

<210> SEQ ID NO 17
<211> LENGTH: 21
<212> TYPE: DNA
<213> ORGANISM: Artificial
<220> FEATURE:
<223> OTHER INFORMATION: Primer, Synthesized

<400> SEQUENCE: 17
gccttttggg tgtgggagat c                                        21

<210> SEQ ID NO 18
<211> LENGTH: 22

<212> TYPE: DNA
<213> ORGANISM: Artificial
<220> FEATURE:
<223> OTHER INFORMATION: Primer, Synthesized

<400> SEQUENCE: 18
tgatggctca aacacagcga cc                                                  22

<210> SEQ ID NO 19
<211> LENGTH: 110
<212> TYPE: PRT
<213> ORGANISM: homo sapiens

<400> SEQUENCE: 19

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 20
<211> LENGTH: 3111
<212> TYPE: DNA
<213> ORGANISM: Artificial
<220> FEATURE:
<223> OTHER INFORMATION: Plasmid, Synthesized

<400> SEQUENCE: 20
gatctcgatc ccgcgaaatt aatacgactc actataggga gaccacaacg gtttccctct      60
agaaataatt ttgtttaact ttaagaagga gatatacata tgggatccat ggtaagcttg     120
aattccgatc cggctgctaa caaagcccga aggaagctg agttggctgc tgccaccgct     180
gagcaataac tagcataacc ccttggggcc tctaaacggg tcttgagggg ttttttgctg     240
aaaggaggaa ctatatccgg ataattcttg aagacgaaag gcctcgtga tacgcctatt     300 tttataggtt aatgtcatga taataatggt ttcttagacg tcaggtggca cttttcgggg     360
aaatgtgcgc ggaaccccta tttgtttatt tttctaaata cattcaaata tgtatccgct     420
catgagacaa taaccctgat aaatgcttca ataatatttt gttaaaattc gcgttaaatt     480
tttgttaaat cagctcattt tttaaccaat aggccgaaat cggcaaaatc ccttataaat     540
caaaagaata gaccgagata gggttgagtg ttgttccagt ttggaacaag agtccactat     600 taagaacgt ggactccaac gtcaagggc gaaaaccgt ctatcagggc gatggcccac     660
tacgtgaacc atcaccctaa tcaagttttt tggggtcgag gtgccgtaaa gcactaaatc     720
ggaaccctaa agggagcccc cgatttagag cttgacgggg aaagccggcg aacgtggcga     780
gaaaggaagg gaagaaagcg aaaggagcgg gcgctagggc gctggcaagt gtagcggtca     840
cgctgcgcgt aaccaccaca cccgccgcgc ttaatgcgcc gctacagggc gcgtcaggtg     900
gcacttttcg gggaaatgtg cgcggaaccc ctatttgttt attttttctaa atacattcaa     960

```
atatgtatcc gctcatgaga caataaccct gataaatgct tcaataatat tgaaaaagga    1020
agagtatgag tattcaacat ttccgtgtcg cccttattcc cttttttgcg gcattttgcc    1080
ttcctgtttt tgctcaccca gaaacgctgg tgaaagtaaa agatgctgaa gatcagttgg    1140
gtgcacgagt gggttacatc gaactggatc tcaacagcgg taagatcctt gagagttttc    1200
gccccgaaga acgttttcca atgatgagca cttttaaagt tctgctatgt ggcgcggtat    1260
tatcccgtgt tgacgccggg caagagcaac tcggtcgccg catacactat tctcagaatg    1320
acttggttga gtactcacca gtcacagaaa agcatcttac ggatggcatg acagtaagag    1380
aattatgcag tgctgccata accatgagtg ataacactgc ggccaactta cttctgacaa    1440
cgatcggagg accgaaggag ctaaccgctt ttttgcacaa catgggggat catgtaactc    1500
gccttgatcg ttgggaaccg gagctgaatg aagccatacc aaacgacgag cgtgacacca    1560
cgatgcctgc agcaatggca acaacgttgc gcaaactatt aactggcgaa ctacttactc    1620
tagcttcccg gcaacaatta atagactgga tggaggcgga taaagttgca ggaccacttc    1680
tgcgctcggc ccttccggct ggctggttta ttgctgataa atctggagcc ggtgagcgtg    1740
ggtctcgcgg tatcattgca gcactggggc cagatggtaa gccctcccgt atcgtagtta    1800
tctacacgac ggggagtcag gcaactatgg atgaacgaaa tagacagatc gctgagatag    1860
gtgcctcact gattaagcat tggtaactgt cagaccaagt ttactcatat atactttaga    1920
ttgatttaaa acttcatttt taatttaaaa ggatctaggt gaagatcctt tttgataatc    1980
tcatgaccaa aatcccttaa cgtgagtttt cgttccactg agcgtcagac cccgtagaaa    2040
agatcaaagg atcttcttga gatccttttt ttctgcgcgt aatctgctgc ttgcaaacaa    2100
aaaaaccacc gctaccagcg gtggtttgtt tgccggatca agagctacca actctttttc    2160
cgaaggtaac tggcttcagc agagcgcaga taccaaatac tgtccttcta gtgtagccgt    2220
agttaggcca ccacttcaag aactctgtag caccgcctac atacctcgct ctgctaatcc    2280
tgttaccagt ggctgctgcc agtggcgata agtcgtgtct taccgggttg gactcaagac    2340
gatagttacc ggataaggcg cagcggtcgg gctgaacggg gggttcgtgc acacagccca    2400
gcttggagcg aacgacctac accgaactga gatacctaca gcgtgagcta tgagaaagcg    2460
ccacgcttcc cgaagggaga aaggcggaca ggtatccggt aagcggcagg gtcggaacag    2520
gagagcgcac gagggagctt ccagggggaa acgcctggta tctttatagt cctgtcgggt    2580
ttcgccacct ctgacttgag cgtcgatttt tgtgatgctc gtcaggggg cggagcctat    2640 ggaaaaacgc cagcaacgcg gcctttttac ggttcctggc cttttgctgg ccttttgctc    2700
acatgttctt tcctgcgtta tcccctgatt ctgtggataa ccgtattacc gcctttgagt    2760
gagctgatac cgctcgccgc agccgaacga ccgagcgcag cgagtcagtg agcgaggaag    2820
cggaagagcg cctgatgcgg tattttctcc ttacgcatct gtgcggtatt tcacaccgca    2880
atggtgcact ctcagtacaa tctgctctga tgccgcatag ttaagccagt atacactccg    2940
ctatcgctac gtgactgggt catggctgcg ccccgacacc cgccaacacc cgctgacgcg    3000
ccctgacggg cttgtctgct cccggcatcc gcttacagac aagctgtgac cgtctccggg    3060
agctgcatgt gtcagaggtt ttcaccgtca tcaccgaaac gcgcgaggca g             3111
```

<210> SEQ ID NO 21
<211> LENGTH: 3342
<212> TYPE: DNA
<213> ORGANISM: Artificial
<220> FEATURE:

<223> OTHER INFORMATION: Plasmid, Synthesized

<400> SEQUENCE: 21

```
gatctcgatc ccgcgaaatt aatacgactc actatagggc gaccacaacg gtttccctct      60
agaaataatt ttgtttaact ttaagaagga gatataatcg atgtctaact cgagtgacaa     120
gtctgtctgc ctattcaccg attttgattc tcaaacaaat gtgtcacaaa gtaaggattc     180
tgatgtgtat atcacagaca aatgtgtgct agacatgagg tctatggact tcaagagcaa     240
cagtgctgtg gcctggagca acaaatctga ctttgcatgt gcaaacgcct tcaacaacag     300
cattattcca gaagacacct tcttccccag cccagaaagt tcctaagctt gaattccgat     360
ccggctgcta acaaagcccg aaaggaagct gagttggctg ctgccaccgc tgagcaataa     420
ctagcataac cccttggggc ctctaaacgg gtcttgaggg gttttttgct gaaggagga     480
actatatccg gataattctt gaagacgaaa gggcctcgtg atacgcctat ttttataggt     540
taatgtcatg ataataatgg tttcttagac gtgaggtggc acttttcggg gaaatgtgcg     600
cggaacccct atttgtttat ttttctaaat acattcaaat atgtatccgc tcatgagaca     660
ataaccctga taaatgcttc aataatattt tgttaaaatt cgcgttaaat ttttgttaaa     720
tcagctcatt ttttaaccaa taggccgaaa tcggcaaaat cccttataaa tcaaaagaat     780
agaccgagat agggttgagt gttgttccag tttggaacaa gagtccacta ttaaagaacg     840
tggactccaa cgtcaaaggg cgaaaaaccg tctatcaggg cgatggccca ctacgtgaac     900
catcacccta atcaagtttt tggggtcga ggtgccgtaa agcactaaat cggaacccta     960
aagggagccc ccgatttaga gcttgacggg gaaagccggc gaacgtggcg agaaaggaag    1020
ggaagaaagc gaaaggagcg ggcgctaggg cgctggcaag tgtagcggtc acgctgcgcg    1080
taaccaccac acccgccgcg cttaatgcgc cgctacaggg cgcgtcaggt ggcacttttc    1140
ggggaaatgt gcgcggaacc cctatttgtt tattttcta aatacattca aatatgtatc    1200
cgctcatgag acaataaccc tgataaatgc ttcaataata ttgaaaaagg aagagtatga    1260
gtattcaaca tttccgtgtc gcccttattc cctttttgc ggcattttgc cttcctgttt    1320
ttgctcaccc agaaacgctg gtgaaagtaa aagatgctga agatcagttg ggtgcacgag    1380
tgggttacat cgaactggat ctcaacagcg gtaagatcct tgagagtttt cgccccgaag    1440
aacgttttcc aatgatgagc acttttaaag ttctgctatg tggcgcggta ttatcccgtg    1500
ttgacgccgg gcaagagcaa ctcggtcgcc gcatacacta ttctcagaat gacttggttg    1560
agtactcacc agtcacagaa aagcatctta cggatggcat gacagtaaga gaattatgca    1620
gtgctgccat aaccatgagt gataacactg cggccaactt acttctgaca acgatcggag    1680
gaccgaagga gctaaccgct tttttgcaca acatggggga tcatgtaact cgccttgatc    1740
gttgggaacc ggagctgaat gaagccatac caaacgacga gcgtgacacc acgatgcctg    1800
cagcaatggc aacaacgttg cgcaaactat taactggcga actacttact ctagcttccc    1860
ggcaacaatt aatagactgg atggaggcgg ataaagttgc aggaccactt ctgcgctcgg    1920
cccttccggc tggctggttt attgctgata aatctggagc cggtgagcgt gggtctcgcg    1980
gtatcattgc agcactgggg ccagatggta agccctcccg tatcgtagtt atctacacga    2040
cggggagtca ggcaactatg gatgaacgaa atagacagat cgctgagata ggtgcctcac    2100
tgattaagca ttggtaactg tcagaccaag tttactcata tatactttag attgatttaa    2160
aacttcattt ttaatttaaa aggatctagg tgaagatcct ttttgataat ctcatgacca    2220
aaatccctta acgtgagttt tcgttccact gagcgtcaga ccccgtagaa aagatcaaag    2280
```

-continued

```
gatcttcttg agatcctttt tttctgcgcg taatctgctg cttgcaaaca aaaaaaccac      2340
cgctaccagc ggtggtttgt tgccggatc aagagctacc aactcttttt ccgaaggtaa       2400
ctggcttcag cagagcgcag ataccaaata ctgtccttct agtgtagccg tagttaggcc      2460
accacttcaa gaactctgta gcaccgccta catacctcgc tctgctaatc ctgttaccag      2520
tggctgctgc cagtggcgat aagtcgtgtc ttaccgggtt ggactcaaga cgatagttac      2580
cggataaggc gcagcggtcg ggctgaacgg ggggttcgtg cacacagccc agcttggagc      2640
gaacgaccta caccgaactg agatacctac agcgtgagct atgagaaagc gccacgcttc      2700
ccgaagggag aaaggcggac aggtatccgg taagcggcag ggtcggaaca ggagagcgca      2760
cgagggagct ccaggggga aacgcctggt atctttatag tcctgtcggg tttcgccacc       2820
tctgacttga gcgtcgattt tgtgatgct cgtcagggg gcggagccta tggaaaaacg        2880
ccagcaacgc ggcctttta cggttcctgg cctttgctg gcctttgct cacatgttct        2940 ttcctgcgtt atcccctgat tctgtggata accgtattac cgcctttgag tgagctgata      3000
ccgctcgccg cagccgaacg accgagcgca gcgagtcagt gagcgaggaa gcggaagagc      3060
gcctgatgcg gtattttctc cttacgcatc tgtgcggtat ttcacaccgc aatggtgcac      3120
tctcagtaca atctgctctg atgccgcata gttaagccag tatacactcc gctatcgcta      3180
cgtgactggg tcatggctgc gccccgacac ccgccaacac ccgctgacgc gccctgacgg      3240
gcttgtctgc tcccggcatc cgcttacaga caagctgtga ccgtctccgg gagctgcatg      3300
tgtcagaggt tttcaccgtc atcaccgaaa cgcgcgaggc ag                         3342
```

<210> SEQ ID NO 22
<211> LENGTH: 3836
<212> TYPE: DNA
<213> ORGANISM: Artificial
<220> FEATURE:
<223> OTHER INFORMATION: Plasmid, Synthesized

<400> SEQUENCE: 22

```
gatctcgatc ccgcgaaatt aatacgactc actataggga gaccacaacg gtttccctct       60
agaaataatt ttgtttaact ttaagaagga gatatacata tgaacgctgg tgtcactcag      120
accccaaaat tccaggtcct gaagacagga cagagcatga cactgcagtg tgcccaggat      180
atgaaccatg aatacatgtc ctggtatcga caagacccag gcatgggggt gaggctgatt      240
cattactcag ttggtgctgg tatcactgac caaggagaag tccccaatgg ctacaatgtc      300
tccagatcaa ccacagagga tttcccgctc aggctgctgt cggctgctcc ctcccagaca      360
tctgtgtact tctgtgccag caggccggga ctagcgggag ggcgaccaga gcagtacttc      420
gggccgggca ccaggctcac ggtcacagag gacctgaaaa acgtgttccc acccgaggtc      480
gctgtgtttg agccatcaga agcagagatc tcccacaccc aaaaggccac actggtgtgc      540
ctggccaccg gtttctaccc cgaccacgtg agctgagct ggtgggtgaa tgggaaggag      600
gtgcacagtg gggtctgcac agacccgcag cccctcaagg agcagcccgc cctcaatgac      660
tccagatacg ctctgagcag ccgcctgagg gtctcggcca ccttctggca ggaccccccgc      720 aaccacttcc gctgtcaagt ccagttctac gggctctcgg agaatgacga gtggaccccag      780 gatagggcca aacccgtcac ccagatcgtc agcgccgagg cctggggtag agcagactaa      840
gcttgaattc cgatccggct gctaacaaag cccgaaagga agctgagttg gctgctgcca      900
ccgctgagca ataactagca taacccctg gggcctctaa acgggtcttg agggggtttttt     960
```

```
tgctgaaagg aggaactata tccggataat tcttgaagac gaaagggcct cgtgatacgc    1020
ctatttttat aggttaatgt catgataata atggtttctt agacgtcagg tggcactttt    1080
cggggaaatg tgcgcggaac ccctatttgt ttattttttct aaatacattc aaatatgtat   1140
ccgctcatga gacaataacc ctgataaatg cttcaataat attttgttaa aattcgcgtt    1200 aaattttttgt taaatcagct catttttttaa ccaataggcc gaaatcggca aaatcccttat  1260 taaatcaaaa gaatagaccg agatagggtt gagtgttgtt ccagtttgga caagagtcc    1320 actattaaag aacgtggact ccaacgtcaa agggcgaaaa accgtctatc agggcgatgg    1380
cccactacgt gaaccatcac cctaatcaag ttttttgggg tcgaggtgcc gtaaagcact    1440
aaatcggaac cctaaaggga gcccccgatt tagagcttga cggggaaagc cggcgaacgt    1500
ggcgagaaag gaagggaaga aagcgaaagg agcgggcgct agggcgctgg caagtgtagc    1560
ggtcacgctg cgcgtaacca ccacacccgc cgcgcttaat gcgccgctac agggcgcgtc    1620
aggtggcact tttcggggaa atgtgcgcgg aaccccctatt tgtttatttt tctaaataca    1680
ttcaaatatg tatccgctca tgagacaata accctgataa atgcttcaat aatattgaaa    1740
aaggaagagt atgagtattc aacatttccg tgtcgccctt attcccttttt ttgcggcatt    1800 ttgccttcct gtttttgctc acccagaaac gctggtgaaa gtaaagatg ctgaagatca     1860 gttgggtgca cgagtgggtt acatcgaact ggatctcaac agcggtaaga tccttgagag    1920
ttttcgcccc gaagaacgtt ttccaatgat gagcactttt aaagttctgc tatgtggcgc    1980
ggtattatcc cgtgttgacg ccgggcaaga gcaactcggt cgccgcatac actattctca    2040
gaatgacttg gttgagtact caccagtcac agaaaagcat cttacggatg gcatgacagt    2100
aagagaatta tgcagtgctg ccataaccat gagtgataac actgcggcca acttacttct    2160
gacaacgatc ggaggaccga aggagctaac cgcttttttg cacaacatgg gggatcatgt    2220
aactcgcctt gatcgttggg aaccggagct gaatgaagcc ataccaaacg acgagcgtga    2280
caccacgatg cctgcagcaa tggcaacaac gttgcgcaaa ctattaactg gcgaactact    2340
tactctagct tcccggcaac aattaataga ctggatggag gcggataaag ttgcaggacc    2400
acttctgcgc tcggcccttc cggctggctg gtttattgct gataaatctg gagccggtga    2460
gcgtgggtct cgcggtatca ttgcagcact ggggccagat ggtaagccct cccgtatcgt    2520
agttatctac acgacgggga gtcaggcaac tatggatgaa cgaaatagac agatcgctga    2580
gataggtgcc tcactgatta agcattggta actgtcagac caagtttact catatatact    2640
ttagattgat ttaaaacttc attttttaatt taaaaggatc taggtgaaga tcctttttga    2700
taatctcatg accaaaatcc cttaacgtga gttttcgttc cactgagcgt cagacccgt     2760 agaaaagatc aaaggatctt cttgagatcc ttttttttctg cgcgtaatct gctgcttgca    2820
aacaaaaaaa ccaccgctac cagcggtggt ttgtttgccg gatcaagagc taccaactct    2880
ttttccgaag gtaactggct tcagcagagc gcagatacca aatactgtcc ttctagtgta    2940
gccgtagtta ggccaccact tcaagaactc tgtagcaccg cctacatacc tcgctctgct    3000
aatcctgtta ccagtggctg ctgccagtgg cgataagtcg tgtcttaccg ggttggactc    3060
aagacgatag ttaccggata aggcgcagcg gtcgggctga acggggggtt cgtgcacaca    3120
gcccagcttg gagcgaacga cctacaccga actgagatac ctacagcgtg agctatgaga    3180
aagcgccacg cttcccgaag ggagaaaggc ggacaggtat ccggtaagcg cagggtcgg    3240 aacaggagag cgcacgaggg agcttccagg gggaaacgcc tggtatcttt atagtcctgt    3300
cgggtttcgc cacctctgac ttgagcgtcg attttttgtga tgctcgtcag gggggcggag    3360
```

```
cctatggaaa acgccagca acgcggcctt tttacggttc ctggccttt  gctggccttt    3420 tgctcacatg ttctttcctg cgttatcccc tgattctgtg ataaccgta ttaccgcctt    3480 tgagtgagct gataccgctc gccgcagccg aacgaccgag cgcagcgagt cagtgagcga    3540
ggaagcggaa gagcgcctga tgcggtattt tctccttacg catctgtgcg gtatttcaca    3600
ccgcaatggt gcactctcag tacaatctgc tctgatgccg catagttaag ccagtataca    3660
ctccgctatc gctacgtgac tgggtcatgg ctgcgcccg acaccgcca  acacccgctg    3720 acgcgccctg acgggcttgt ctgctcccgg catccgctta cagacaagct gtgaccgtct    3780
ccgggagctg catgtgtcag aggttttcac cgtcatcacc gaaacgcgcg aggcag       3836
```

<210> SEQ ID NO 23
<211> LENGTH: 3341
<212> TYPE: DNA
<213> ORGANISM: Artificial
<220> FEATURE:
<223> OTHER INFORMATION: Plasmid, Synthesized

<400> SEQUENCE: 23

```
gatctcgatc ccgcgaaatt aatacgactc actataggga gaccacaacg gtttccctct     60
agaaataatt ttgtttaact ttaagaagga gatatacata tgtctaactc gagtgacaag    120
tctgtctgcc tattcaccga ttttgattct caaacaaatg tgtcacaaag taaggattct    180
gatgtgtata tcacagacaa atgtgtgcta gacatgaggt ctatggactt caagagcaac    240
agtgctgtgg cctggagcaa caaatctgac tttgcatgtg caaacgcctt caacaacagc    300
attattccag aagacacctt cttccccagc ccagaaagtt cctaagcttg aattccgatc    360
cggctgctaa caaagcccga aggaagctg  agttggctgc tgccaccgct gagcaataac    420
tagcataacc ccttggggcc tctaaacggg tcttgagggg ttttttgctg aaaggaggaa    480
ctatatccgg ataattcttg aagacgaaag ggcctcgtga tacgcctatt tttataggtt    540
aatgtcatga taataatggt ttcttagacg tcaggtggca cttttcgggg aaatgtgcgc    600
ggaaccccta tttgtttatt tttctaaata cattcaaata tgtatccgct catgagacaa    660
taaccctgat aaatgcttca ataatatttt gttaaaattc gcgttaaatt tttgttaaat    720
cagctcattt tttaaccaat aggccgaaat cggcaaaatc ccttataaat caaaagaata    780
gaccgagata gggttgagtg ttgttccagt ttggaacaag agtccactat taagaacgt    840 ggactccaac gtcaaagggc gaaaaaccgt ctatcagggc gatggcccac tacgtgaacc    900 atcacctaa  tcaagttttt tggggtcgag gtgccgtaaa gcactaaatc ggaaccctaa    960
agggagcccc cgatttagag cttgacgggg aaagccggcg aacgtggcga gaaaggaagg    1020
gaagaaagcg aaaggagcgg cgctagggc  gctggcaagt gtagcggtca cgctgcgcgt    1080
aaccaccaca cccgccgcgc ttaatgcgcc gctacagggc gcgtcaggtg cacttttcg    1140 gggaaatgtg cgcggaaccc ctatttgttt attttttctaa atacattcaa atatgtatcc    1200
gctcatgaga caataaccct gataaatgct tcaataatat tgaaaaagga agagtatgag    1260
tattcaacat ttccgtgtcg cccttattcc cttttttgcg gcattttgcc ttcctgtttt    1320
tgctcaccca gaaacgctgg tgaaagtaaa agatgctgaa gatcagttgg gtgcacgagt    1380
gggttacatc gaactggatc tcaacagcgg taagatcctt gagagttttc gccccgaaga    1440
acgttttcca atgatgagca cttttaaagt tctgctatgt ggcgcggtat tatcccgtgt    1500
tgacgccggg caagagcaac tcggtcgccg catacactat tctcagaatg acttggttga    1560
```

```
gtactcacca gtcacagaaa agcatcttac ggatggcatg acagtaagag aattatgcag    1620
tgctgccata accatgagtg ataacactgc ggccaactta cttctgacaa cgatcggagg    1680
accgaaggag ctaaccgctt ttttgcacaa catgggggat catgtaactc gccttgatcg    1740
ttgggaaccg gagctgaatg aagccatacc aaacgacgag cgtgacacca cgatgcctgc    1800
agcaatggca acaacgttgc gcaaactatt aactggcgaa ctacttactc tagcttcccg    1860
gcaacaatta atagactgga tggaggcgga taaagttgca ggaccacttc tgcgctcggc    1920
ccttccggct ggctggttta ttgctgataa atctggagcc ggtgagcgtg ggtctcgcgg    1980
tatcattgca gcactggggc cagatggtaa gccctcccgt atcgtagtta tctacacgac    2040
ggggagtcag gcaactatgg atgaacgaaa tagacagatc gctgagatag gtgcctcact    2100
gattaagcat tggtaactgt cagaccaagt ttactcatat atactttaga ttgatttaaa    2160
acttcatttt taatttaaaa ggatctaggt gaagatcctt tttgataatc tcatgaccaa    2220
aatcccttaa cgtgagtttt cgttccactg agcgtcagac cccgtagaaa agatcaaagg    2280
atcttcttga tccttttt ttctgcgcgt aatctgctgc ttgcaaacaa aaaaaccacc    2340
gctaccagcg gtggtttgtt tgccggatca agagctacca actctttttc cgaaggtaac    2400
tggcttcagc agagcgcaga taccaaatac tgtccttcta gtgtagccgt agttaggcca    2460
ccacttcaag aactctgtag caccgcctac atacctcgct ctgctaatcc tgttaccagt    2520
ggctgctgcc agtggcgata gtcgtgtct taccgggttg gactcaagac gatagttacc    2580
ggataaggcg cagcggtcgg gctgaacggg gggttcgtgc acacagccca gcttggagcg    2640
aacgacctac accgaactga gatacctaca gcgtgagcta tgagaaagcg ccacgcttcc    2700
cgaagggaga aaggcggaca ggtatccggt aagcggcagg gtcggaacag gagagcgcac    2760
gagggagctt ccaggggaa acgcctggta tctttatagt cctgtcggt ttcgccacct    2820 ctgacttgag cgtcgatttt tgtgatgctc gtcagggggg cggagcctat ggaaaaacgc    2880
cagcaacgcg gcctttttac ggttcctggc cttttgctgg ccttttgctc acatgttctt    2940
tcctgcgtta tcccctgatt ctgtggataa ccgtattacc gcctttgagt gagctgatac    3000
cgctcgccgc agccgaacga ccgagcgcag cgagtcagtg agcgaggaag cggaagagcg    3060
cctgatgcgg tattttctcc ttacgcatct gtgcggtatt tcacaccgca atggtgcact    3120
ctcagtacaa tctgctctga tgccgcatag ttaagccagt atacactccg ctatcgctac    3180
gtgactgggt catggctgcg ccccgacacc cgccaacacc cgctgacgcg ccctgacggg    3240
cttgtctgct cccggcatcc gcttacagac aagctgtgac cgtctccggg agctgcatgt    3300
gtcagaggtt ttcaccgtca tcaccgaaac gcgcgaggca g                       3341
```